United States Patent
Armato III et al.

(10) Patent No.: US 6,813,375 B2
(45) Date of Patent: Nov. 2, 2004

(54) AUTOMATED METHOD AND SYSTEM FOR THE DELINEATION OF THE CHEST WALL IN COMPUTED TOMOGRAPHY SCANS FOR THE ASSESSMENT OF PLEURAL DISEASE

(75) Inventors: Samuel G. Armato III, Downers Grove, IL (US); Heber MacMahon, Chicago, IL (US); Geoffrey R. Oxnard, Chicago, IL (US)

(73) Assignee: University of Chicago, Chicago, IL (US)

( * ) Notice: Subject to any disclaimer, the term of this patent is extended or adjusted under 35 U.S.C. 154(b) by 15 days.

(21) Appl. No.: 10/292,625

(22) Filed: Nov. 13, 2002

(65) Prior Publication Data

US 2003/0086599 A1 May 8, 2003

Related U.S. Application Data

(63) Continuation-in-part of application No. 09/881,002, filed on Jun. 15, 2001, now Pat. No. 6,577,752.

(51) Int. Cl.$^7$ .............................................. G06K 9/00
(52) U.S. Cl. ...................... 382/131; 382/132; 382/169; 382/171
(58) Field of Search ................................ 382/128, 129, 382/130, 131, 132, 133, 172, 199, 266; 600/407, 408, 409, 411, 716, 301, 538, 203.12, 204.23; 128/898, 899, 922

(56) References Cited

U.S. PATENT DOCUMENTS

| | | | | |
|---|---|---|---|---|
| 5,319,549 A | | 6/1994 | Katsuragawa et al. | 382/108 |
| 5,572,565 A | | 11/1996 | Abdel-Mottaleb | 378/37 |
| 5,638,458 A | * | 6/1997 | Giger et al. | 382/132 |
| 5,707,352 A | * | 1/1998 | Sekins et al. | 604/509 |
| 5,776,063 A | * | 7/1998 | Dittrich et al. | 600/408 |
| 5,850,465 A | * | 12/1998 | Shimura et al. | 382/132 |
| 6,139,505 A | | 10/2000 | Murphy | 600/532 |
| 6,141,437 A | * | 10/2000 | Xu et al. | 382/130 |
| 6,246,784 B1 | * | 6/2001 | Summers | 382/128 |
| 6,282,307 B1 | * | 8/2001 | Armato et al. | 382/132 |
| 6,287,290 B1 | | 9/2001 | Perkins et al. | 604/516 |
| 6,345,112 B1 | * | 2/2002 | Summers et al. | 382/128 |
| 6,483,934 B2 | | 11/2002 | Armato, III et al. | 382/132 |

* cited by examiner

Primary Examiner—Jayanti K. Patel
Assistant Examiner—Abolfazl Tabatabai
(74) Attorney, Agent, or Firm—Oblon, Spivak, McClelland, Maier & Neustadt, P.C.

(57) ABSTRACT

A method, system, and computer program product for automated and semi-automated measurements of pleural space and/or pleural thickening in thoracic CT images to identify the presence and quantify the extent of pleura-based disease, including obtaining a CT image including the pleural space and/or the pleural thickening, segmenting lungs in the obtained image, obtaining an initial endpoint on a chest wall or a mediastinum boundar; determining a terminal endpoint on a boundary of the at least one segmented lung; and determining a distance between said initial endpoint and said the terminal endpoint as the extent of the pleural space and/or the pleural thickening. Exemplary embodiments include determining the extent of pleural space and/or pleural thickening based on linear distance, area, and volume of the space between the lung boundary and at least one of the chest wall and the mediastinum boundary. These pleural determinations may be used to quantify the extent of disease in a particular case as additional information to be incorporated into a radiologist's decision-making process, or as part of a computer-aided diagnostic scheme that alerts radiologists of the potential for pleural disease in the case.

22 Claims, 21 Drawing Sheets

FIG. 3B
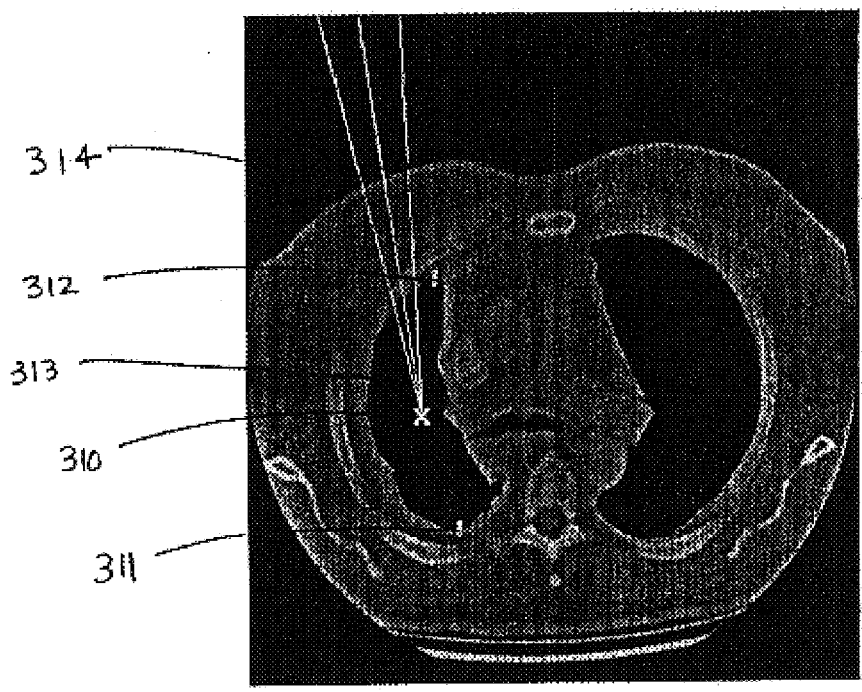
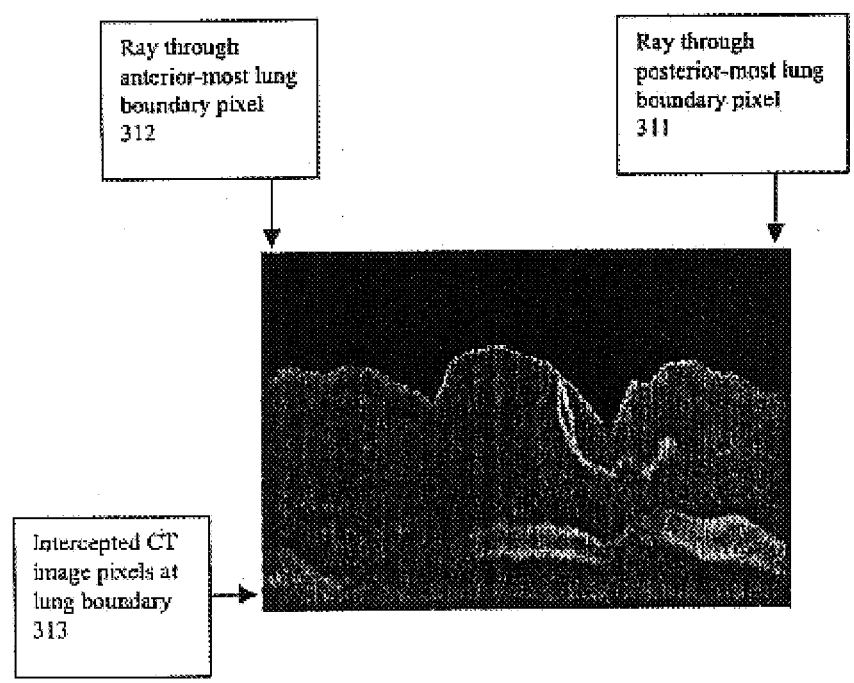
FIG. 3C

Original Image                Chest Wall Image
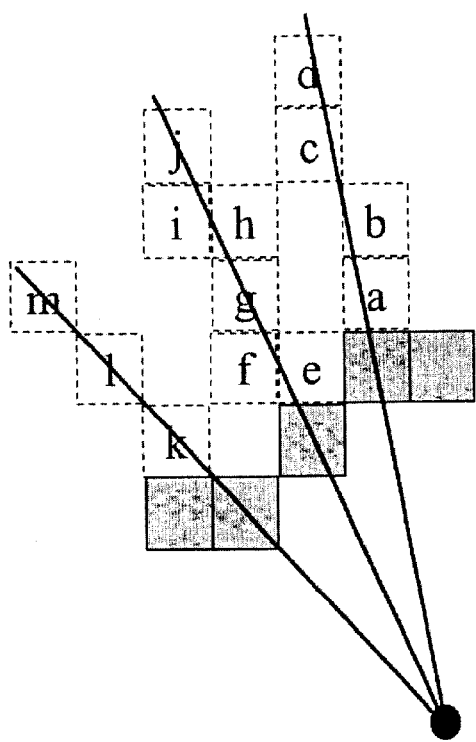
| | | j | | |
| | | i | | |
| | d | h | | |
| | c | g | m | |
| | b | f | l | |
| | a | e | k | |
lung centroid
FIG. 4A                       FIG. 4B

```
< Geometric parameters of RIGHT RIBS >
-- ordered from anterior to posterior --
----------------------------------------
Rib  Xcent  Ycent  Area   Pleural thickness
1    139    197    217.0  6.6 mm
2    78     316    465.0  13.5 mm
3    143    408    756.5  11.8 mm
```

```
< Geometric parameters of LEFT RIBS >
-- ordered from anterior to posterior --
----------------------------------------
Rib  Xcent  Ycent  Area   Pleural thickness
1    347    162    404.5  1.6 mm
2    439    279    700.5  1.4 m
3    365    407    662.0  5.1 mm
```

FIG. 8

AUTOMATED METHOD AND SYSTEM FOR THE DELINEATION OF THE CHEST WALL IN COMPUTED TOMOGRAPHY SCANS FOR THE ASSESSMENT OF PLEURAL DISEASE

CROSS-REFERENCE TO RELATED APPLICATIONS

The present application is a continuation-in-part of U.S. application Ser. No. 09/881,002, filed Jun. 15, 2001, now Pat. No. 6,577,752. The contents of that application are incorporated herein by reference.

The present invention was made in part with U.S. Government support under grant number CA83908 from the USPHS. The U.S. Government may have certain rights to this invention.

BACKGROUND OF THE INVENTION

FIELD OF THE INVENTION

The invention relates generally to the computerized, automated assessment of computed tomography (CT) or magnetic resonance (MR) scans (or images), and more particularly, to methods, systems, and computer program products for delineating the chest wall in helical CT or MR scans of the thorax to assess pleural disease.

The present invention also generally relates to computerized techniques for automated analysis of digital images, for example, as disclosed in one or more of U.S. Pat. Nos. 4,839,807; 4,841,555; 4,851,984; 4,875,165; 4,907,156; 4,918,534; 5,072,384; 5,133,020; 5,150,292; 5,224,177; 5,289,374; 5,319,549; 5,343,390; 5,359,513; 5,452,367; 5,463,548; 5,491,627; 5,537,485; 5,598,481; 5,622,171; 5,638,458; 5,657,362; 5,666,434; 5,673,332; 5,668,888; 5,732,697; 5,740,268; 5,790,690; 5,832,103; 5,873,824; 5,881,124; 5,931,780; 5,974,165; 5,982,915; 5,984,870; 5,987,345; 6,011,862; 6,058,322; 6,067,373; 6,075,878; 6,078,680; 6,088,473; 6,112,112; 6,138,045; 6,141,437; 6,185,320; 6,205,348 as well as U.S. patent application Ser. Nos. 08/173,935; 08/398,307 (PCT Publication WO 96/27846); Ser. Nos. 08/536,149; 08/900,188; 08/900,189; 09/027,468; 09/028,518; 09/092,004; 09/121,719; 09/141,535; 09/471,088; 09/692,218; 09/716,335; 09/759,333; 09/760,854; 09/773,636; 09/816,217; 09/830,562; and 09/830,574 and PCT patent applications PCT/US00/41299; PCT/US01/00680; PCT/US01/01478 and PCT/US01/01479, all of which are incorporated herein by reference.

The present invention includes use of various technologies referenced and described in the above-noted U.S. Patents and Applications, as well as described in the references identified in the following LIST OF REFERENCES by the author(s) and year of publication and cross-referenced throughout the specification by reference to the respective number, in parentheses, of the reference:

LIST OF REFERENCES

1. Ng C S, Munden R F, Libshitz H I. Malignant pleural mesothelioma: The spectrum of manifestations on CT in 70 cases. *Clinical Radiology* 54:415–421, 1999.
2. Sterman D H, Kaiser L R, Albelda S M. Advances in the treatment of malignant pleural mesothelioma. *Chest* 116:504–520, 1999.
3. Huo Z, Giger M L, Vyborny C J, Bick U, Lu P, Wolverton D E, Schmidt R A. Analysis of spiculation in the computerized classification of mammographic masses. *Medical Physics* 22:1569–1579, 1995.
4. Jiang Y, Nishikawa R M, Wolverton D E, Metz C E, Giger M L, Schmidt R A, Vyborny C J, Doi K. Malignant and benign clustered microcalcifications: Automated feature analysis and classification. *Radiology* 201:581–582, 1996.
5. Giger M L, Doi K, MacMahon H, Nishikawa R M, Hoffmann K R, Vybomy C J, Schmidt R A, Jia H, Abe K, Chen X, Kano A, Katsuragawa S, Yin F-F, Alperin N, Metz C E, Behlen F M, Sluis D. An "intelligent" workstation for computer-aided diagnosis. *RadioGraphics* 13:647–656, 1993.
6. Xu X-W, Doi K, Kobayashi T, MacMahon H, Giger M L. Development of an improved CAD scheme for automated detection of lung nodules in digital chest images. *Medical Physics* 24:1395–1403, 1997.
7. Katsuragawa S, Doi K, MacMahon H, Monnieir-Cholley L, Ishida T, Kobayashi T. Classification of normal and abnormal lungs with interstitial diseases by rule-based method and artificial neural networks. *Journal of Digital Imaging* 10:108–114, 1997.
8. Difazio M C, MacMahon H, Xu X-W, Tsai P, Shiraishi J, Armato S G, III, Doi K. Digital chest radiography: Effect of temporal subtraction images on detection accuracy. *Radiology* 202:447–452, 1997.
9. Armato S G, III, Giger M L, MacMahon H. Automated detection of lung nodules in CT scans: Preliminary results. *Medical Physics* (in press), 2001.
10. Webb W R, Brant W E, Helms C A. *Fundamentals of Body CT*. Philadelphia, Pa.: W. B. Saunders Company; 1998.
11. Giger M L, Bae K T, MacMahon H. Computerized detection of pulmonary nodules in computed tomography images. *Investigative Radiology* 29:459–465, 1994.
12. Sonka M, Hlavac V, Boyle R. *Image Processing, Analysis, and Machine Vision*. Pacific Grove, Calif.: Brooks/Cole Publishing Company; 1999.
13. Armato S G, III, Giger M L, Moran C J, Doi K, MacMahon H. Computerized detection of lung nodules in computed tomography scans. In: K Doi, H MacMahon, M L Giger, and K R Hoffmann, eds. *Computer-Aided Diagnosis in Medical Images*. Amsterdam: Elsevier Science; 1999:119–123.
14. Armato S G, III, Giger M L, Blackburn J T, Doi K, MacMahon H. Three-dimensional approach to lung nodule detection in helical CT. *SPIE Proceedings* 3661:553–559, 1999.
15. Armato S G, III, Giger M L, Moran C J, MacMahon H, Doi K. Automated detection of pulmonary nodules in helical computed tomography images of the thorax. *SPIE Proceedings* 3338:916–919, 1998.
16. Fitzgibbon A W, Pilu M, Fisher R B. Direct least squares fitting of ellipses. In: eds. *International Conference on Pattern Recognition*. Vienna: IEEE Computer Society; 1996.
17. Mathews J H. *Numerical Methods for Mathematics, Science, and Engineering*. Englewood Cliffs, N.J.: Prentice Hall; 1992.
18. Sahiner B, Chan H-P, Petrick N, Helvie M A, Goodsitt M M. Computerized characterization of masses on mammograms: The rubber band straightening transform and texture analysis. *Medical Physics*, 25:516–526, 1998.
19. Fiebich M, Tomiak M M, Engelmann R M, McGill J, Hoffmann K R. Computer assisted diagnosis in CT angiography of abdominal aortic aneurysms. *Proc SPIE*, 3034: 86, 1997.

DISCUSSION OF THE BACKGROUND

Malignant pleural mesothelioma is diagnosed in approximately 2000–3000 people in the Unites States each year (see Reference 1) and is associated with an extremely poor prognosis. Given the correlation of mesothelioma with asbestos exposure and a latency of up to 35–40 years (see Reference 1), the incidence of malignant mesothelioma is expected to rise over the next decade or two. Although numerous attempts to develop an accepted treatment for the management of mesothelioma patients have been largely unsuccessful, investigators continue to explore novel chemotherapy agents and multimodality treatment programs in an effort to reduce morbidity and, potentially, prolong the survival of patients afflicted with this disease (see Reference 2).

Computed tomography (CT) has been a major advance in the diagnosis and assessment of mesothelioma. Moreover, CT is an important tool for monitoring a patient's response to treatment in a variety of clinical trials. The increased use of CT in the evaluation of mesothelioma demands new, computerized image analysis methodologies to facilitate extraction of the image features that are most relevant to the characterization of mesothelioma. Image processing and computer vision techniques have been developed for the detection and classification of breast masses and microcalcifications on mammograms (see References 3–5), for the detection of lung nodules and interstitial disease on chest radiographs (see References 6, 7), for the enhanced visualization of temporal change on sequential chest radiographs (see Reference 8), and for the detection of lung nodules in thoracic CT scans (see Reference 9). The evaluation of mesothelioma could benefit from similar techniques that would assist radiologists and clinicians in the reliable, consistent, and reproducible quantification of mesothelioma.

While currently no standard exists for radiologic measurement of mesothelioma, one protocol indicates manual measurement of up to three areas of the pleural rind at each of three levels (i.e., three separate CT sections). To accomplish this task, a radiologist holds a ruler up to the CT film, makes the appropriate measurement, and uses a scale printed on the film to convert the measurement of the image into the real-world size of the measured structure. More accurate and global assessment of mesothelioma certainly requires the acquisition of many more than nine measurements (i.e., three measurements on each of three CT sections).

However, the amount of effort required to accomplish this task with the current manual procedure places a practical limit on the number of measurements that may be acquired.

SUMMARY OF THE INVENTION

Accordingly, an object of this invention is to provide an improved method, system, and computer program product for the automated measurements of pleural space and pleural thickening in thoracic CT or MR scans, including automated segmentation of lungs in thoracic CT or MR scans, automated construction of a "chest wall image" from thoracic CT or MR scans, automated and semi-automated identification (segmentation) of ribs in thoracic CT or MR scans, and automated delineation of the chest wall in thoracic CT or MR scans.

These and other objects are achieved by way of a method, system, and computer program product constructed according to the present invention, wherein pleural disease (particularly mesothelioma, a pleura-based cancer) is assessed in thoracic CT or MR scans acquired with either a standard helical protocol or a low-dose helical protocol by measuring pleural space and pleural thickening in the CT or MR scans.

In particular, according to one aspect of the present invention, there is provided a novel method, system, and computer program product for determining an extent of at least one of a pleural space and a pleural thickening, including the steps of obtaining an image including at least one of the pleural space and the pleural thickening; segmenting at least one lung in the obtained image; obtaining an initial endpoint on one of a chest wall and a mediastinum boundary; determining a terminal endpoint on a boundary of the at least one segmented lung; and determining a distance between said initial endpoint and said terminal endpoint as the extent of the at least one of the pleural space and the pleural thickening.

In addition, according to another aspect of the present invention, there is provided a novel method, system, and computer program product for determining an extent of at least one of a pleural space and a pleural thickening, comprising: obtaining an image including at least one of the pleural space and the pleural thickening; segmenting at least one lung in the obtained image; selecting at least one pixel on one of a chest wall and a mediastinum boundary; determining a contour of the one of the chest wall and the mediastinum boundary based on the at least one pixel on the one of the chest wall and the mediastinum boundary; and calculating an area between a boundary of the at least one segmented lung and the contour of the one of the chest wall and the mediastinum boundary as the extent of the at least one of the pleural space and the pleural thickening.

In addition, according to still another aspect of the present invention, there is provided a novel method, system, and computer program product for assessing pleural disease, including the steps of obtaining an image including the pleural space and/or the pleural thickening, segmenting lungs in the obtained image, constructing a chest wall image from the obtained image using a lung boundary obtained in the segmenting step and a series of normal rays extending away from the lung boundary, identifying ribs in the chest wall image, mapping a location of the identified ribs back into the obtained image, and determining in the obtained image the extent of the pleural space and/or the pleural thickening between the identified ribs mapped back into the obtained image and at least one segmented lung.

According to another aspect of the present invention, the terminal endpoint is selected to be a pixel on the boundary of the at least one segmented lung for which a distance between the pixel and the initial endpoint is minimum.

According to another aspect of the present invention, the terminal endpoint is selected to be a pixel on the boundary of the at least one segmented lung that lies on a line connecting the initial endpoint with a center-of-mass of the at least one segmented lung.

According to another aspect of the present invention, there is provided a method for selecting, as the terminal endpoint, a pixel on the boundary of the at least one segmented lung for which a distance between the pixel and the initial endpoint is maximum, the pixel being located within a predetermined distance of the initial endpoint.

According to another aspect of the present invention, there is provided a method for determining the terminal endpoint, comprising the steps of determining a set of candidate terminal endpoints as those pixels on the boundary of the at least one segmented lung having an associated normal line that extends within a predetermined number of pixels of the initial endpoint; and selecting, as the terminal endpoint, a pixel from the set of candidate terminal endpoints for which the associated normal line is most closely aligned with a line from the initial endpoint to a center-of-mass of the at least one segmented lung.

According to another aspect of the present invention, there is provided a method for determining the terminal endpoint, comprising the steps of constructing a set of lines passing through the initial endpoint at different angles; determining a standard deviation of gray levels of a predetermined number of pixels on each line in the set of lines; selecting, as a tangent line, a line in the set of lines having a smallest standard deviation, as determined in the preceding determining step; and selecting, as the terminal endpoint, a pixel on the boundary of the at least one segmented lung that lies on a line normal to the tangent line selected in the preceding selecting step.

According to another aspect of the present invention, there is provided a novel system implementing the method of the invention.

According to still another aspect of the present invention, there is provided a novel computer program product, included within a computer readable medium of a computer system, which upon execution causes the computer system to perform the method of the invention.

According to still another aspect of the present invention, the system for determining an extent of at least one of a pleural space and a pleural thickening includes graphical user interface having a display controller configured to display a representation of the extent of the at least one of the pleural space and the pleural thickening. The display controller may include one or more control sections configured to perform various functions related to determining an extent of at least one of a pleural space and a pleural thickening. For example, there is provided a first control section configured to display at least one measurement of the extent of the at least one of the pleural space and the pleural thickening obtained by at least one observer. Moreover, there is provided a second control section configured to display a plurality of measurements of the extent of the at least one of the pleural space and the pleural thickening obtained at a plurality of different times, and a third control section configured to compare a plurality of measurements of the extent of the at least one of the pleural space and the pleural thickening obtained by a plurality of observers.

In addition, the system of the present invention includes a device configured to store the at least one measurement of the extent of the at least one of the pleural space and the pleural thickening obtained by at least one observer. Further, the system includes a display configured to display a representation of the extent of the at least one of the pleural space and the pleural thickening.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3B shows the geometry for constructing the chest wall image according to the method of FIG. 3A based on the results of automated lung segmentation;

FIG. 3C shows an exemplary chest wall image for the right hemithorax, and the relationship between the rows and columns of the chest wall image and pixels in the original image, as a result of the method of FIG. 3A;

FIG. 4A is an exemplary illustration of the construction of the chest wall image based on the lung centroid (obtained from automated lung segmentation), the lung boundary (obtained from automated lung segmentation), and rays drawn from the lung centroid through individual lung boundary pixels in a CT or MR image;

FIG. 4B illustrates the corresponding chest wall image resulting from the image of FIG. 4A;

FIG. 8 shows an exemplary computerized pleural space measurement output according to the present invention;

DETAILED DESCRIPTION OF THE PREFERRED EMBODIMENTS

Figure 1:
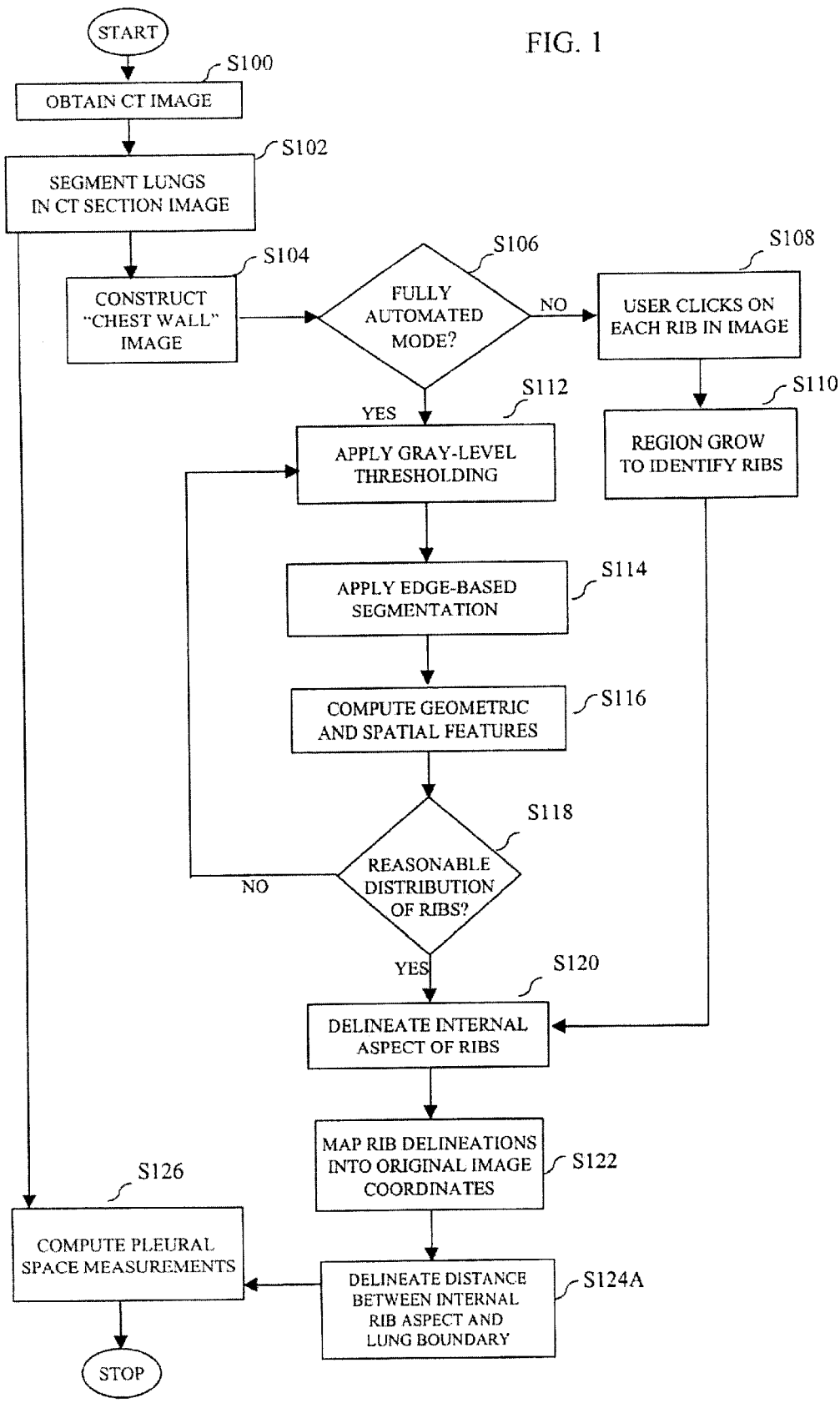
FIG. 1 is a flowchart of a first embodiment according to the present invention, illustrating a method for the delineation of the chest wall and for the measurement of pleural space and/or pleural thickening in thoracic CT or MR scans based on a distance between lung boundary and chest wall.

Referring now to the drawings, wherein like reference numerals designate identical or corresponding parts throughout the several views, FIG. 1 is a flowchart of a method for the measurement of the pleural space and/or the pleural thickening in thoracic CT or MR scans. The overall scheme includes an initial acquisition of CT or MR image data in step S100. For each section image, gray-level thresholding techniques are used to segment the lungs in step S102 (to be described later). A segmented lung region and its boundary serve two purposes: (1) the center-of-mass (centroid) of the segmented lung region and the set of lung boundary pixels obtained from the segmented lung region are used to construct a "chest wall image," in step S104 (to be described later), in which rib segmentation is performed, and (2) the lung boundary is combined with the delineated chest wall, which is based on rib segmentation, to provide pleural space measurements in step S126 (to be described later). The pleural space measurements include pleural space and pleural thickening.

Next, rib segmentation is performed by either of two modes: (1) semi-automated mode and (2) fully automated mode. After the chest wall image is constructed in step S104, an inquiry is made in step S106 as to whether the semi-automated or fully automated mode will be used.

If the semi-automated mode is used, the user is shown a CT or MR section image through a graphical user interface. The basic function of such an interface is to provide a "window" that allows a radiologist or clinician to view all the images of a complete CT or MR scan. The interface has a pull-down list from which the user selects the CT or MR scan of interest. Buttons and slider bars allow the user to raster through the individual CT or MR section images, adjust the contrast and brightness of the images, and zoom in on specific regions. The next layer of functionality facilitates user interaction in the semi-automated method for pleural disease assessment. In this mode, the interface prompts the user to position the cursor, using a mouse or a touch-screen, over a rib.

Since an internal aspect of a rib (i.e., the boundary of each rib closest to the lung boundary, where the lung boundary is represented by the bottom row of the chest wall image) is used to represent the chest wall, in step S108, the user manually selects a rib by a single mouse click, for example. This manual selection may be implemented in at least the following ways. The user may select (i.e., click on) a point that lies along the internal aspect of the rib. Or the user may select any point within a rib. The selected point, the "seed point," is mapped into the chest wall image, and a gray-level-based region-growing operation is performed in step S110 to identify the complete rib as it appears in the chest wall image. Region growing identifies all pixels within a local neighborhood of the manually selected seed point that contain gray levels within a certain range of the gray level of the seed point, thus achieving rib segmentation through a semi-automated technique that requires minimal manual input (see Reference 19). The result is a "segmented rib."

If the fully automated mode is used, image processing techniques are applied to the chest wall image to segment ribs. A gray-level threshold is applied to the chest wall image in step S112 so that only the brightest structures (i.e., the bones) in the chest wall image remain. The appropriate gray-level threshold is selected dynamically based on the distribution of gray-level values in the particular chest wall image. Edge-based segmentation methods such as a Sobel filter or a Laplacian operator (see Reference 12) are used in step S114 to complement the degree of rib segmentation achieved with gray-level-thresholding. Geometric characteristics such as eccentricity, circularity, and major axis orientation along with spatial characteristics such as distance from the lung boundary and distribution along the lung boundary are calculated in step S116 and used in step S118 to more definitively identify ribs and exclude other anatomic structures that may also satisfy the gray-level threshold and edge-based methods, thereby ensuring that all the ribs, and only the ribs, are identified in the thresholded chest wall image. For example, to eliminate non-rib structures from the chest wall image, a size criterion may be used to eliminate the small portions of scapula that remain in the thresholded chest wall image. In addition, a distance-from-the-lung-boundary parameter (i.e., a distance-from-the-bottom-of-the-image parameter) is implemented to prevent the entire scapula from being incorrectly identified as a rib. In addition, in step S118, to ensure that all ribs are segmented, the chest wall image is horizontally partitioned into compartments. Based on the observation that ribs tend to be roughly equally spaced in the chest wall image, the presence of an identified rib in each compartment is determined. If a compartment does not contain a portion of what is determined to be a rib, a less-strict gray-level threshold is applied to the pixels within that compartment. This process of lowering the gray-level threshold is repeated iteratively beginning with step S112 until a rib is identified or until some predetermined number of iterations has been reached, in which case it is determined that the compartment does not contain a rib.

After the ribs are segmented by either the semi-automated or the fully automated mode, the internal aspect of the segmented ribs is delineated in step S120. That is, a pixel along the internal aspect of the segmented rib and centered between the ends of the rib is automatically identified. This pixel is mapped to a corresponding pixel in the original CT image in step S122, where the corresponding pixel becomes the pixel upon which pleural space measurements are made. (See FIG. 6 and rib boundary pixels 610.)

Next, a line between each internal rib aspect and the lung boundary is displayed in step S124A, where the length of the line (or linear distance) indicates the pleural thickness at that position. The linear distance is measured in step S126 based on a rib pixel along the internal aspect of each rib using the lung segmentation result of step S102 superimposed with the rib segmentation result of step S124A. A linear measurement is made automatically between the rib pixel and the lung boundary to replicate the mesothelioma measurement method currently used by radiologists. (See FIG. 7 and linear lines 710.) Several variations on this distance measurement are possible. All variations involve the length of a line extending from the rib pixel to the lung boundary. First, the length of a line extending from the rib pixel to that lung boundary pixel closest to the rib pixel may be used to represent the pleural space measurement at that rib position. Second, the length of a line extending from the rib pixel to intersect the lung boundary perpendicularly may be used to represent the pleural space measurement. Third, the length of a line extending perpendicular to the internal aspect of the rib from the rib pixel to the lung boundary may be used. Different ones of these metrics may be applicable under different lung boundary/chest wall spatial relationships. The numeric data may then be presented in tabular form on a level-by-level basis at individual rib positions or as an average of all rib positions selected in a given hemithorax at one level in step S126. (See FIG. 8.)

In the semi-automated mode, if the line between the internal rib aspect and the lung boundary does not, in the opinion of the user, represent an accurate estimation of the pleural thickness at that position, the user may manually draw a line with the graphical user interface to override the semi-automated measurement. When the user has completed a scan, a report of pleural space measurements is generated.

Figure 2A:
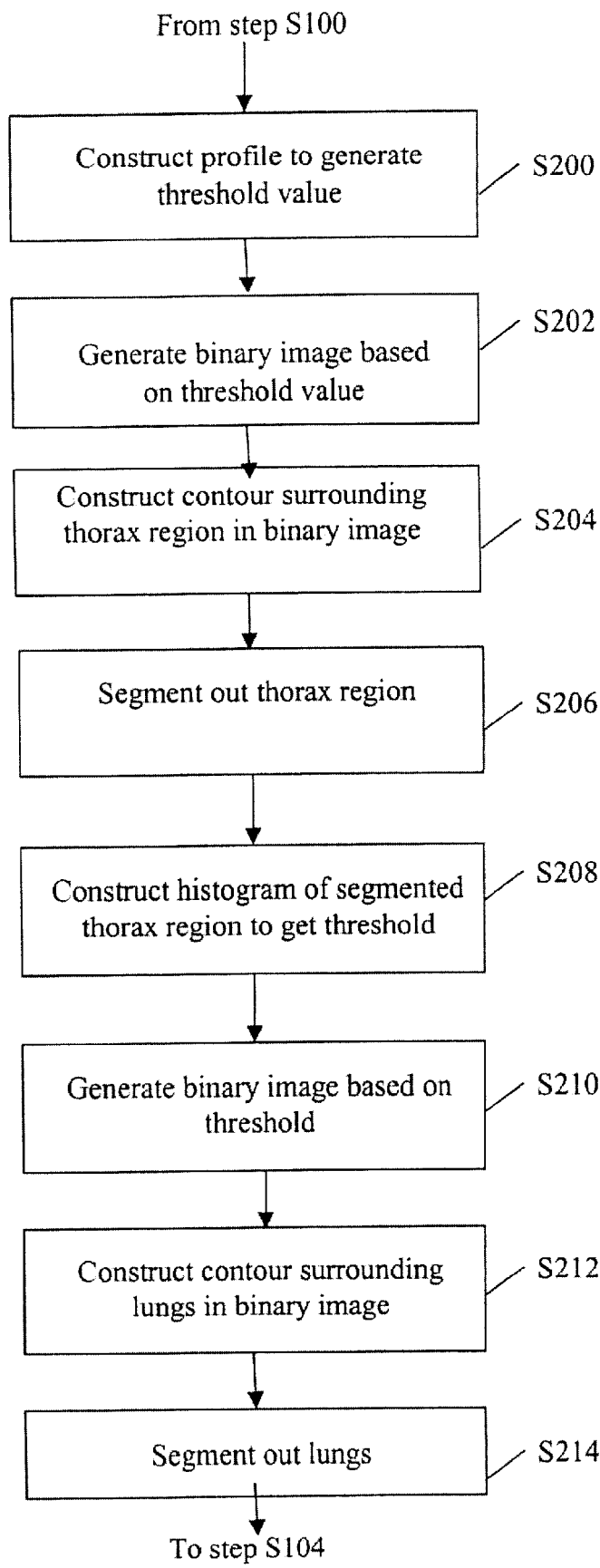
FIG. 2A is a flowchart of an automated lung segmentation method as shown in FIG. 1 according to the present invention.

FIG. 2A is a flowchart of the automated lung segmentation of step S102 in FIG. 1. To segment the lungs, the thorax is first segmented by constructing a cumulative gray-level profile from the values of pixels that lie along the diagonal that extends from a corner of the image to the image center, where the shape of this profile is analyzed to identify a single gray level as a threshold value in step S200 (see Reference 11). In step S202, a binary image is created by thresholding the section image such that a pixel is turned "on" in the binary image if the value of the corresponding pixel in the section image has a value greater than the gray-level threshold; all other pixels remain "off" in the binary image.

An eight-point contour detection scheme (see Reference 12) is used in step S204 to construct a contour surrounding the outermost boundary of the largest "on" region in the binary image (i.e., the thorax). The set of pixels in the section image that lie within this contour defines the segmented thorax region and is used to create a thorax segmentation image such that pixels within the segmented thorax region maintain their original value, in step S206. In addition, in step S206, pixels not included within the segmented thorax region are assigned a value of 0. Pixels that represent portions of the examination table that may be included within the segmented thorax region are identified and eliminated. And, the trachea and main bronchi are segmented based on a region-growing technique (see Reference 12) and eliminated from the segmented thorax region.

After the thorax region is segmented, initial lung segmentation begins for a particular section by constructing a gray-level histogram in step S208 from the pixels that lie within the segmented thorax region (see References 11, 13). The distribution of pixels in this typically bimodal histogram is used to identify a single gray level as a threshold value within the broad minimum in the histogram (see Reference 11). In step S210, a binary image is created by thresholding the thorax segmentation image such that a pixel is turned "on" in the binary image if the value of the corresponding pixel in the thorax segmentation image has a value less than the gray-level threshold; all other pixels remain "off" in the binary image. The presence of a single "on" region that spans both sides of the resulting binary image indicates that gray-level thresholding has "fused" the two lungs and that an anterior junction line is present in the section image. This anterior junction line is automatically delineated as part of step S210 based on the location of a "cleft point" in the binary image and local maximum gray-level information. Pixels along the anterior junction line are turned "off" to ensure the segmentation of two distinct lung regions.

In step S212, an eight-point contour detection scheme (see Reference 12) is used to construct contours surrounding the outermost boundaries of the two largest "on" regions in the binary image (i.e., the lungs). The sets of pixels in the section image that lie within these contours define the segmented lung regions and are used to create a lung segmentation image such that pixels within the segmented lung regions maintain their original value, in step S214. In addition, in step S214, pixels not included within the segmented lung regions are assigned a value of 0. A rolling ball algorithm (see References 14, 15) is applied to rectify the erroneous exclusion of dense structures such as juxta-pleural nodules and hilar vessels. And, to prevent pixels that belong to the diaphragm from contributing to the segmented lung regions, diaphragm analysis is performed both on the initial binary images created from gray-level thresholding and in conjunction with the rolling ball technique.

Figure 2B:
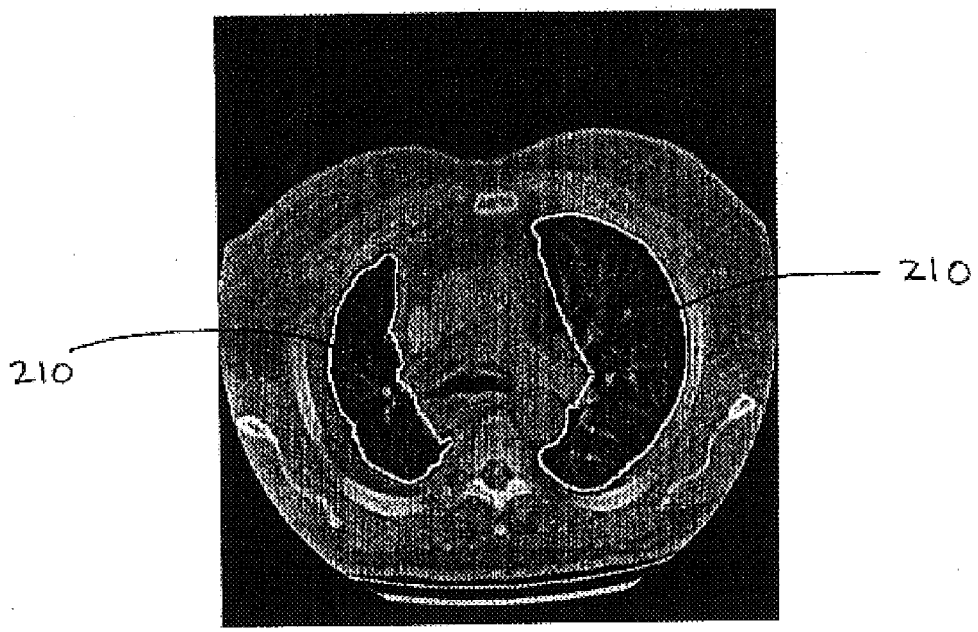
FIG. 2B shows the boundaries of the automatically extracted segmented lung regions as a result of the method of FIG. 2A superimposed on the original section image with mesothelioma in the right hemithorax.

FIG. 2B shows an exemplary result of automated lung segmentation for one CT section image demonstrating mesothelioma in the right hemithorax. The contours 210 superimposed on the original CT image represent the outermost boundaries of the segmented lung regions. These computer-determined lung boundaries provide the basis for many of the subsequent analyses.

With the lung regions segmented as described in FIG. 2A and the lung boundaries identified as the perimeters of the segmented lung regions, rib segmentation is performed next to estimate the position of the chest wall beginning with construction of the chest wall image.

Figure 3A:
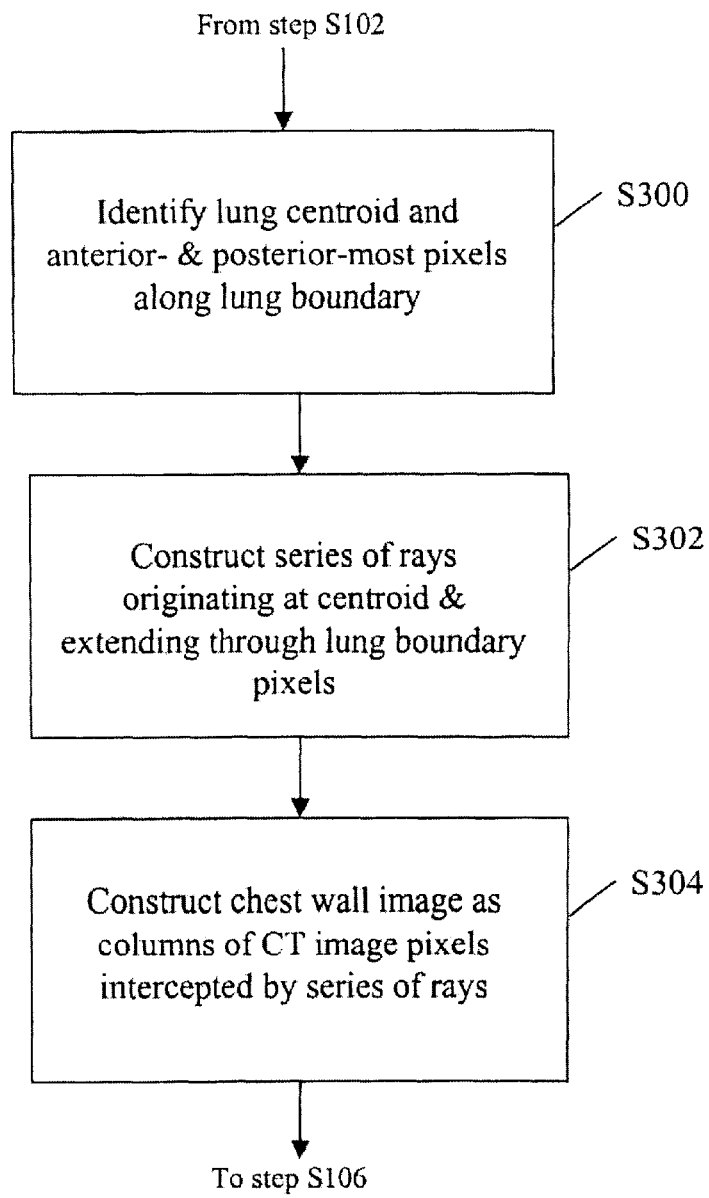
FIG. 3A is a flowchart of a method to construct a chest wall image as shown in FIG. 1 according to the present invention.

FIG. 3A is a flowchart of the chest wall image construction of step S104 of FIG. 1. FIGS. 3B and 3C show exemplary results of the chest wall image construction of FIG. 3A. In step S300 of FIG. 3A, the center-of-mass (centroid) of a lung (indicated by an "x" 310 in FIG. 3B) is identified based on the automated lung segmentation of FIG. 2A, and the anterior-most (i.e., uppermost) and posterior-most (i.e., lowermost) pixels along the lung boundary 313 are identified (indicated by the vertical hash marks 312 and 311, respectively, in FIG. 3B). Next, a series of rays is constructed originating at the lung center-of-mass and extending through each pixel along the lung boundary in step S302. Three such (non-adjacent) rays 314 are depicted in FIG. 3B.

The CT or MR image pixels that are intercepted by a ray contribute to one column of the chest wall image, as shown schematically in FIGS. 4A and 4B. Therefore, since one ray is constructed through each lung boundary pixel (i.e. the gray pixels in FIG. 4A) that exists between the anterior-most and posterior-most lung pixels, the chest wall image is constructed in step S304 of FIG. 3A to include a number of columns equal to the number of corresponding lung boundary pixels. Of the image pixels, only intercepted image pixels that are beyond (i.e., outside of) the lung boundary contribute to the chest wall image (FIG. 4B). Accordingly, the first row of the chest wall image represents the image pixels at the lung boundary, while subsequently higher rows in the chest wall image represent progressively more peripheral pixels as shown in FIG. 3C. Alternatively, the first row of the chest wall image may represent the lung boundary pixels, the second row may represent the image pixels at the lung boundary, and subsequent rows may represent progressively more peripheral pixels. Thus, the chest wall image effectively provides a representation of extrapulmonary anatomy "unwrapped" about the lung boundary (see Reference 18) as shown in FIG. 3C. It should be noted that the chest wall image does not capture extrapulmonary anatomy along the mediastinal aspect of the lung boundary, although a "mediastinum image" may be constructed in a similar manner.

Figure 3D:
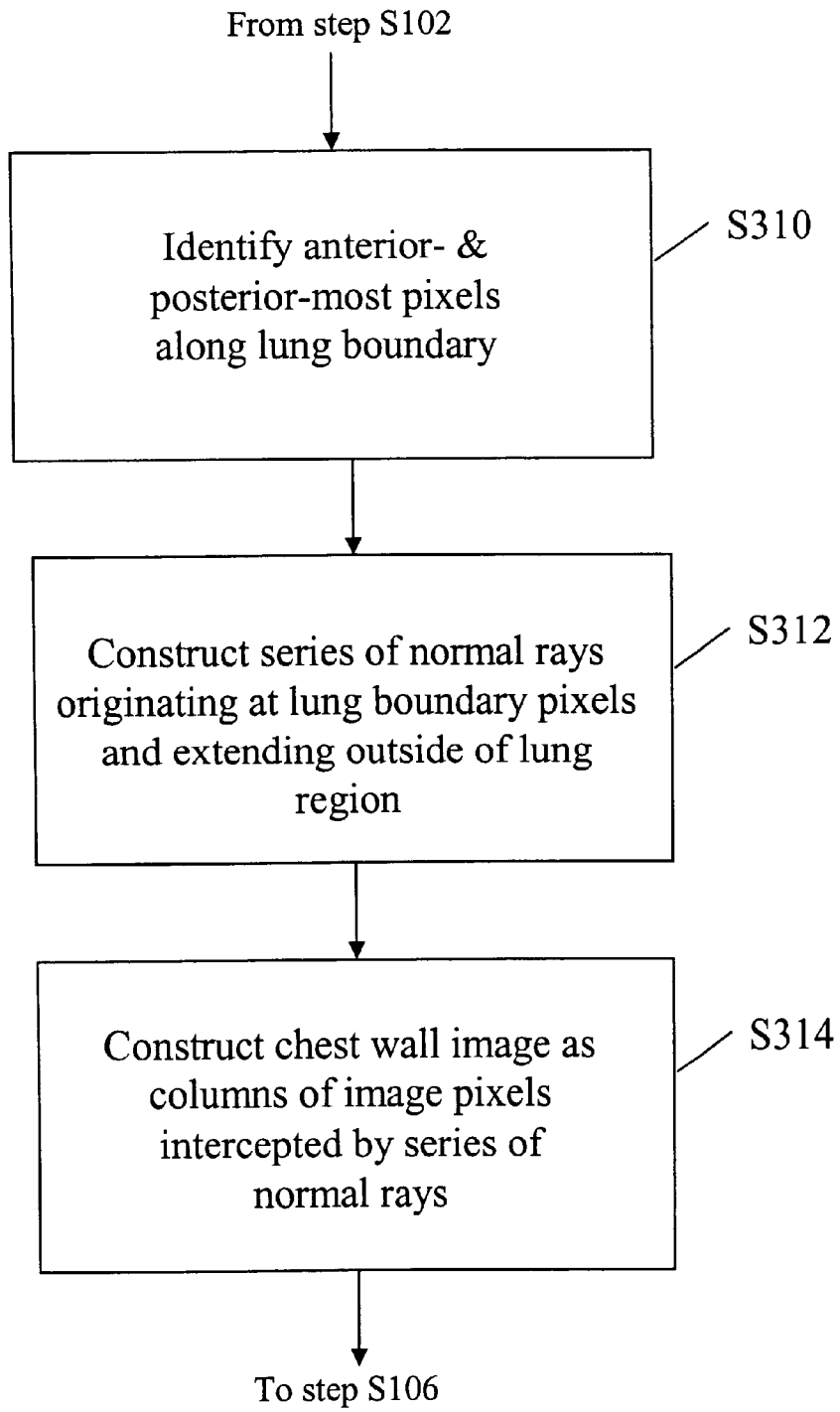
FIG. 3D is a flowchart of a second method to construct a chest wall image as shown in FIG. 1 according to the present invention.

FIG. 3D is a flowchart of an alternative chest wall image construction method executed in step S104 of FIG. 1. In this embodiment, the chest wall image is constructed in a manner analogous to method illustrated in FIGS. 3A, 3B, 3C, 4A, and 4B, except that the centroid of the lung region is not used to construct the series of rays. Instead, a series of normal rays extending outward from the lung boundary is constructed. First, in step S310, the anterior- and posterior-most pixels along the lung boundary are identified. In step S312, for each pixel along the lung boundary nearest the chest wall between the anterior- and posterior-most pixels, a tangent line is determined using the location of those lung boundary pixels that are adjacent to a given lung boundary pixel. For each local tangent line, a ray is then constructed that is normal to the tangent line, originates at the given lung boundary pixel, and extends outward from the lung region. Finally, in step S314, the chest wall image is constructed as columns of image pixels intercepted by the series of normal rays, in a manner analogous to that shown in FIGS. 4A and 4B.

Figure 5A:
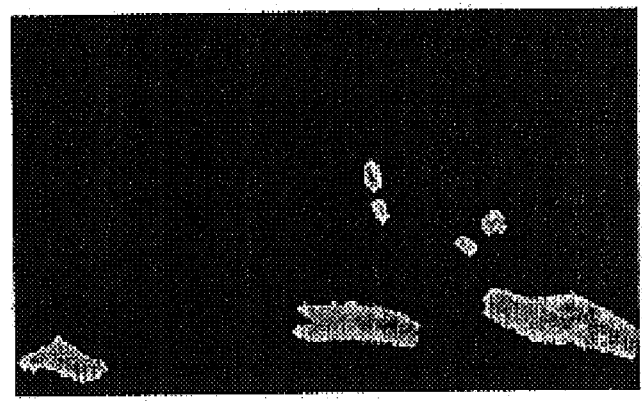
FIG. 5A shows a gray-level thresholded chest wall image indicating how the ribs may be segmented from surrounding anatomy according to the present invention.
Figure 5B:
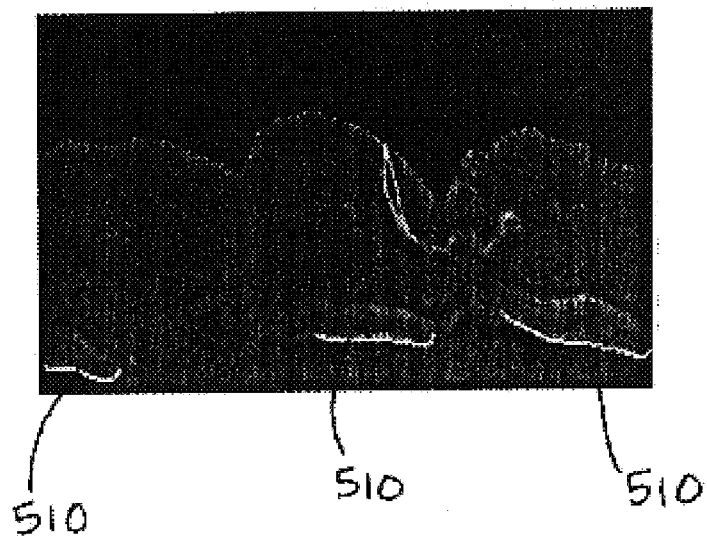
FIG. 5B shows the internal aspects of the ribs as identified from the regions in FIG. 5A superimposed on the original chest wall image of FIG. 3C.

FIG. 5A shows an exemplary rib segmentation in which only the ribs are displayed in the chest wall image according to the method described in FIG. 1. FIG. 5B shows an exemplary delineation of the segmented ribs in FIG. 5A, where the delineated pixels 510 represent the rib boundary pixels closest to the lung boundary as described in step S120 of FIG. 1. The internal aspect of each rib is delineated by selecting the single "on" pixel in each column that is closest to the bottom of the chest wall image.

Figure 6:
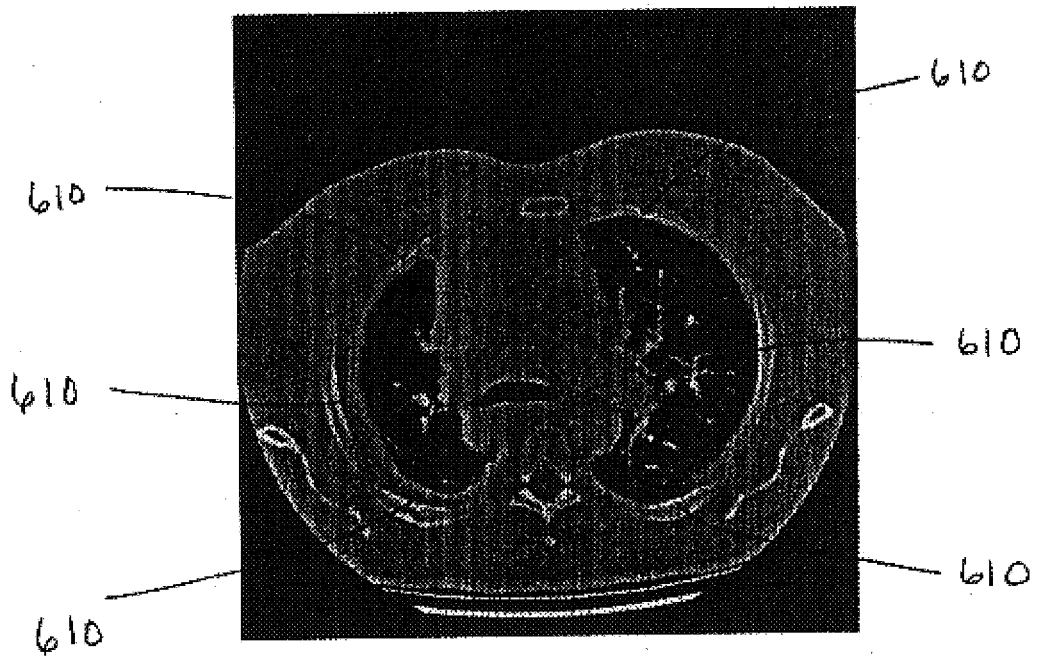
FIG. 6 demonstrates the mapping of internal rib aspect points back into original image coordinates so that the internal aspects of the ribs are now delineated in the original CT or MR image.

FIG. 6 shows exemplary rib boundary pixels 610 that are mapped from the chest wall image back into the coordinate system of the original CT or MR image as described in step S122 of FIG. 1. This method of rib segmentation for the purpose of automatically obtaining the internal aspects of the ribs shown in FIG. 6 has been developed based on a database of CT scans from mesothelioma patients.

Figure 7:
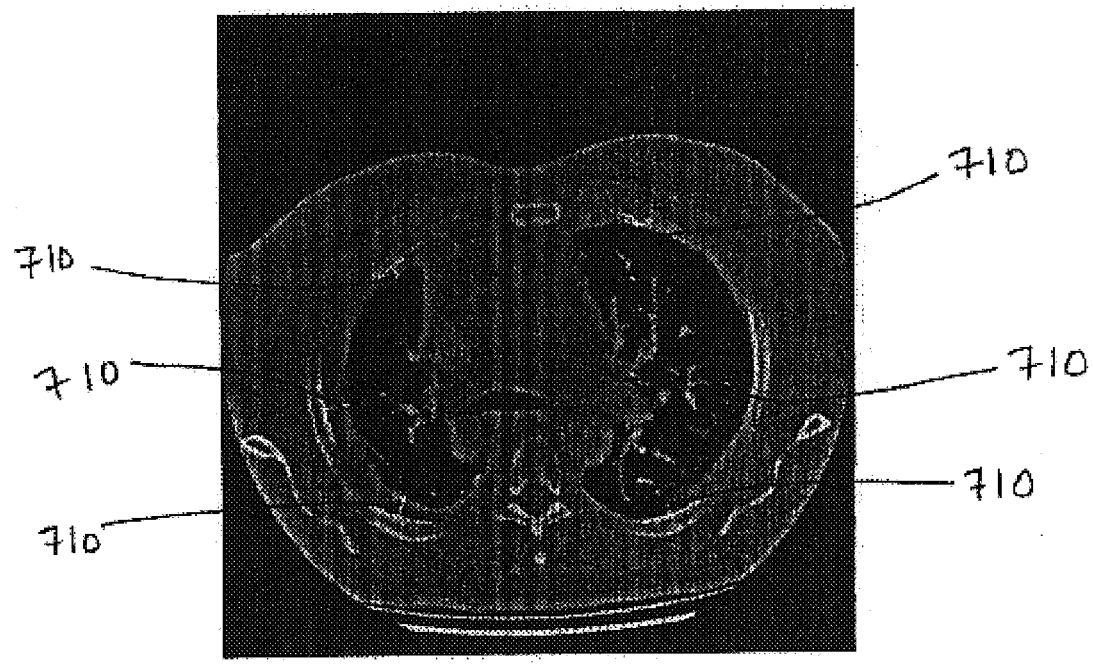
FIG. 7 shows the internal aspects of the ribs with lines extending perpendicularly from the middle point of each rib delineation to the lung boundary indicating a distance metric to measure pleural space and/or pleural thickening according to the present invention.

FIG. 7 shows exemplary lengths of lines 710 extending perpendicular to the internal aspect of the rib from the middle rib pixel of the internal aspect delineation to the lung boundary as described in step S124A of FIG. 1. As previously discussed, different ones of these line metrics may be applicable under different lung boundary/chest wall spatial relationships.

FIG. 8 shows exemplary results of the pleural space measurements of step S126 in FIG. 1 in tabular form on a level-by-level basis at individual rib positions or as an average of all rib positions selected in a given hemithorax at one level. The pleural thickness data correspond to the lengths of the perpendicular lines 710 of FIG. 7. Note that the pleural thicknesses computed for the diseased right hemithorax are substantially greater than the pleural thicknesses computed for the normal left hemithorax.

Figure 9A:
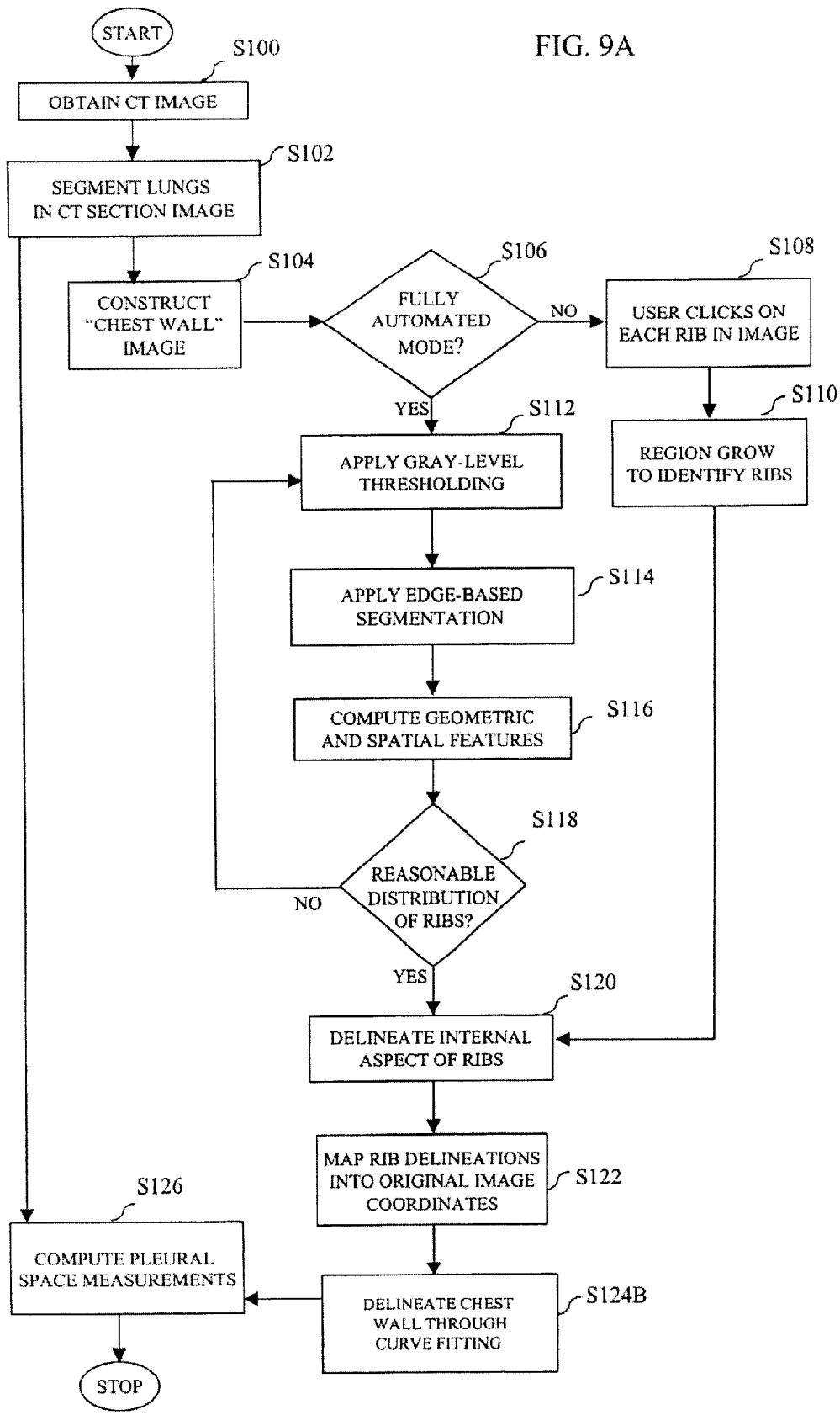
FIG. 9A is a flowchart of a second embodiment according to the present invention in which the pleural space and/or the pleural thickening is measured based on a geometric area between lung boundary and chest wall.

FIG. 9A shows another embodiment of the present invention, in which the pleural space measurement is based on the area of the pleural space and/or the pleural thickening between the anterior-most and posterior-most pixels of the lung. The steps of FIG. 9A are the same as the steps of FIG. 1 with the exceptions that step S124B replaces step 124A and step S126 performs different computations for pleural space measurement. In step S124B, the chest wall is delineated by using curve-fitting (e.g., polynomials or ellipses (see Reference 16)) or interpolation (e.g., cubic splines (see Reference 17)) based on the points along the internal aspects of the ribs in a hemithorax, from which a quantification of the area between the lung boundary and the chest wall delineation can be made. To compute the area of the pleural space and/or the pleural thickening in step S126, the number of pixels between the lung boundary and the chest wall is determined, and a conversion from number of pixels to area (in mm$^2$) is performed.

Figure 9B:
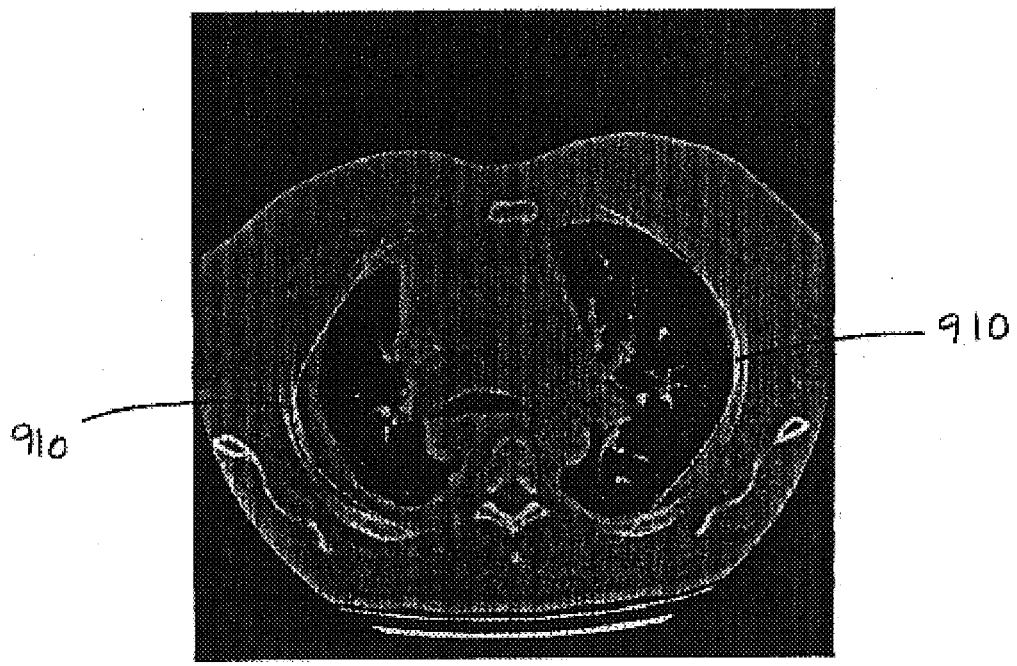
FIG. 9B illustrates how a curve-fitting technique, according to the method of FIG. 9A, applied to the internal rib aspect pixels in the right and left hemithoraces is used to delineate the right and left chest wall, respectively.
Figure 9C:
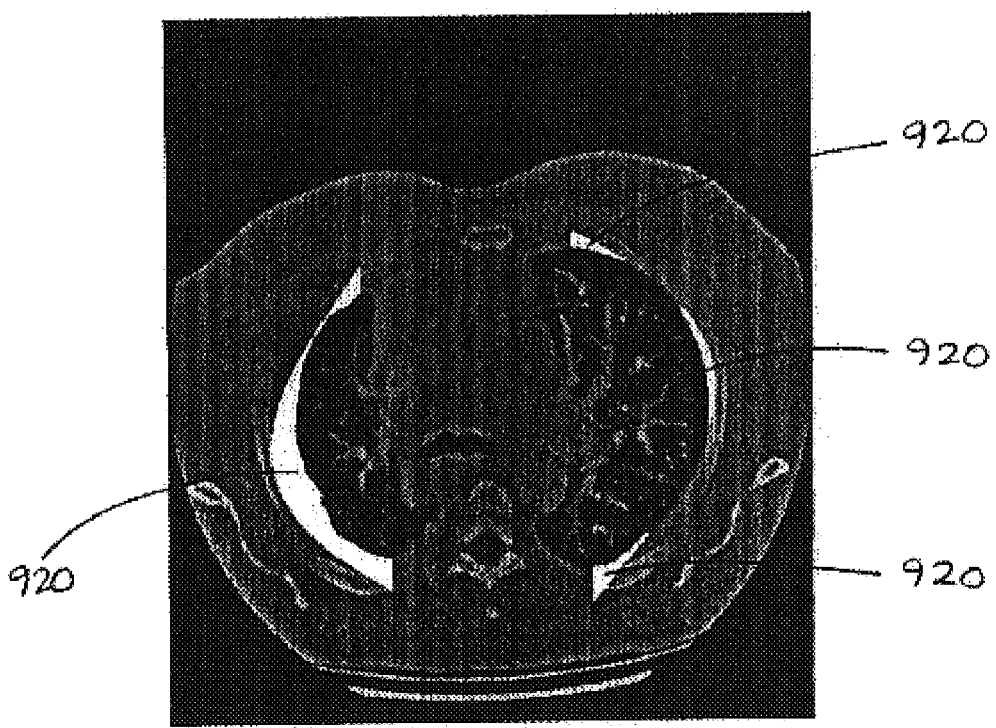
FIG. 9C shows the pixels determined to exist within the pleural space and/or the pleural thickening based on the lung boundary and the chest wall delineation, i.e., the geometric area associated with the pleural space and/or the pleural thickening computed based on these pleural-space pixels, according to the method of FIG. 9A.

FIG. 9B shows an exemplary result of the chest wall delineation 910 of step S124B in FIG. 9A. FIG. 9C shows the pixels 920 between the lung boundary and the chest wall delineation, i.e., the pixels within the pleural space and/or pleural thickening as determined in step S126. A comparison between the pleural-space area of the two hemithoraces in a CT or MR section is then possible to assess the presence or absence of pleural disease.

Figure 10:
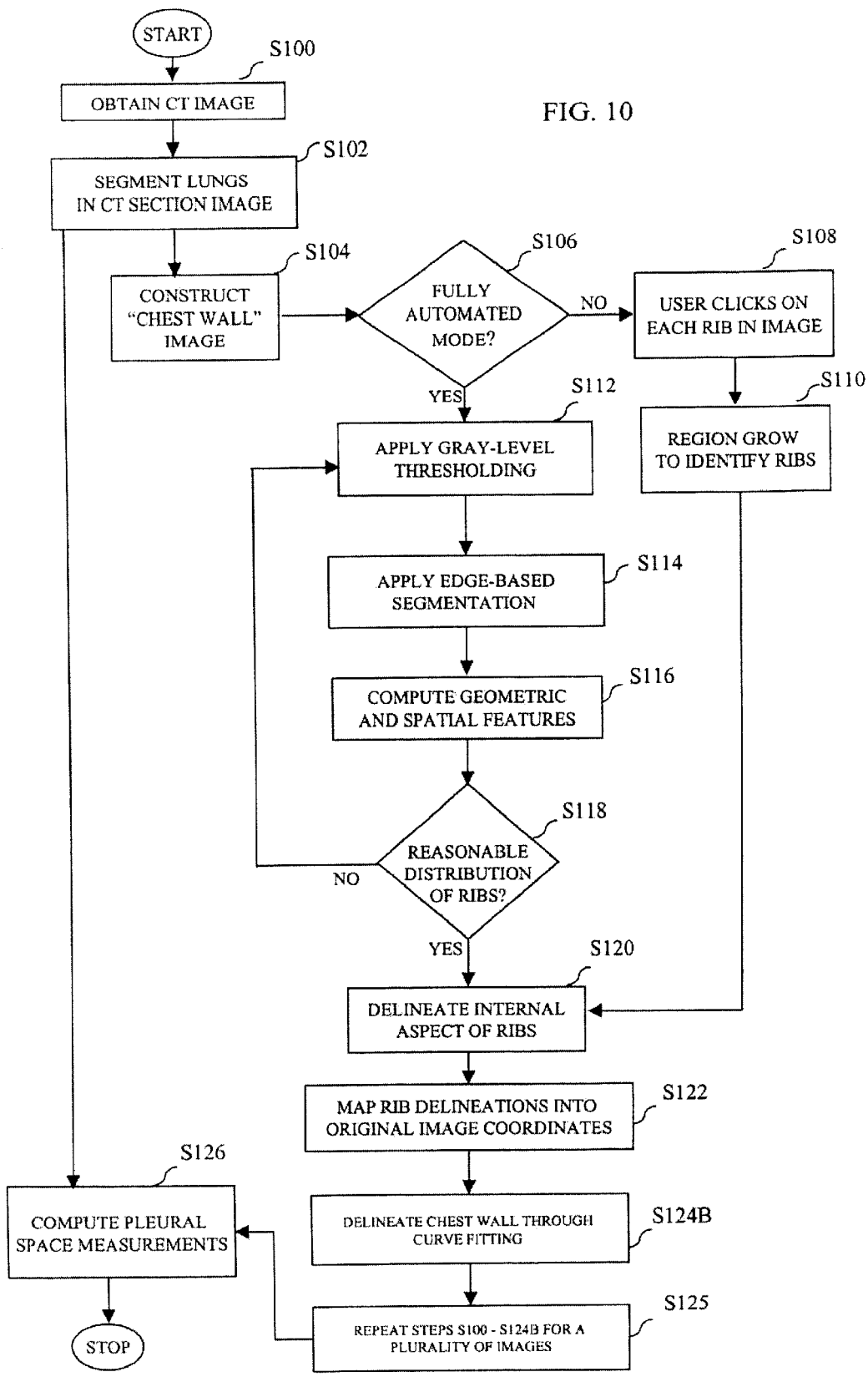
FIG. 10 is a flowchart of a third embodiment according to the present invention in which the pleural space and/or the pleural thickening is measured based on a geometric volume between lung boundary and chest wall.

FIG. 10 is a flowchart of still another embodiment of the present invention in which the complete volume of the pleural space and/or the pleural thickening is calculated. The steps of FIG. 10 are the same as the steps of FIG. 1 with the exceptions that step S124B replaces step 124A and step S126 performs different computations for the pleural space measurement. In step S124B, as in FIG. 9A, the chest wall is delineated by using curve-fitting (e.g., polynomials or ellipses (see Reference 16)) or interpolation (e.g., cubic splines (see Reference 17)) based on the points along the internal aspects of the ribs in a hemithorax, from which a quantification of the area between the lung boundary and the chest wall delineation can be made. Steps S100 through S124B are repeated for each of a plurality of CT or MR images, as stated in step S125. After the chest wall is delineated in each of the CT or MR images, then, in step S126, the pleural space measurement for each of the CT or MR images is computed as an area similar to that calculated in FIG. 9A. Then, the complete volume of the two hemithoraces is computed based on an integration of all measurements made, i.e. the areas, within the sections of the entire plurality of CT or MR images. These measurements may be used to calculate the pleural space measurement in step S126 and to quantify the extent of disease in a particular case as additional information to be incorporated into a radiologist's decision-making process, or the measurements may be used as part of a computer-aided diagnosis process that alerts radiologists of the potential for pleura-based disease in the case.

It is to be understood that the linear distance, area, and volume parameters of FIGS. 1, 9A, and 10, respectively, may be used individually or in combination to compute the pleural space measurements of the present invention.

Figure 13:
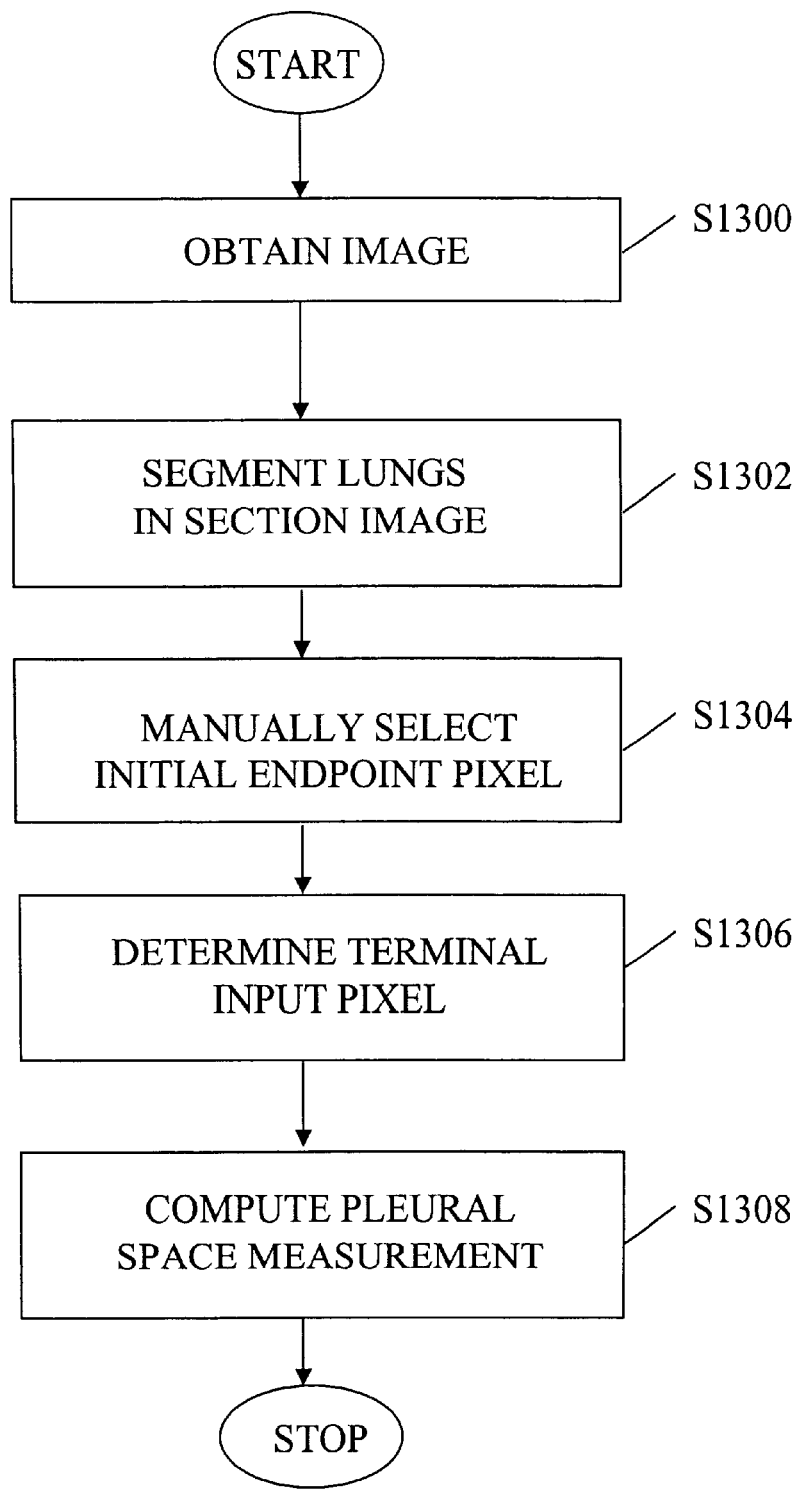
FIG. 13 is a flowchart of a fourth embodiment according to the present invention in which measurements of mesothelioma are obtained through a semi-automated approach, allowing pleural space measurement around the entire lung, rather than solely along the chest wall.

FIG. 13 illustrates another embodiment of the present invention, in which the measurement of mesothelioma is obtained through a semi-automated approach, allowing pleural space measurement around the entire lung, rather than solely along the chest wall. The overall scheme includes an initial acquisition of CT or MR image data in step S1300, which is identical to image acquisition step S1100 described above with regard to FIGS. 1, 9A, and 10. Next, for each section image, gray-level thresholding techniques are used to segment the lungs in step S1302. Note that step S1302 is identical to the lung segmenting step S102 described above with regard to FIGS. 2A and 2B.

In step S1304, a pixel on the chest wall or the boundary of the mediastinum is manually selected to serve and as initial endpoint of a line segment that will be constructed to indicate the thickness of a mesothelioma tumor or some other pleural disease. The selection of the initial endpoint is accomplished using a graphical user interface, which was developed to facilitate the softcopy visualization of CT scans.

The graphical user interface was designed to allow manual as well as semi-automated measurement of structures in the images with a mouse-driven or touch-screen-driven tool. After loading the individual section images from a CT scan, the user rasters through the stack of sections to identify the section or sections that contain structures to be measured.

In manual mode, a "measurement" is obtained from the length (in millimeters) of a line segment constructed within the image by the user using a mouse, touch-screen, or other appropriate input device. For example, the initial endpoint of a line segment is placed when the user clicks the mouse at the desired image location. A magnification window then appears centered at the initial endpoint; this magnification window follows the cursor as the user drags the mouse to create a visible line segment extending from the initial endpoint. The terminal endpoint is then established when the user releases the mouse button to fix the line segment within the image. At the user's discretion, the endpoints of created line segments may be individually moved, or a line segment may be deleted entirely. Any number of line segments may be created in this manner within any number of sections. The corresponding lengths of the line segments are displayed through the interface, and data about each line segment (length, section number, and coordinates of the initial and terminal endpoints) are stored (e.g., on the local hard drive or a network drive). The capability to store and retrieve these measurements allows for the comparison of measurements among observers and across temporally sequential scans.

In both manual and semi-automated modes, the user of the interface clicks on a point along the chest wall or boundary of the mediastinum in step S1304.

In step S1306, the terminal endpoint is selected manually, as discussed above, or the system automatically connects the selected point with the lung boundary and provides a pleural rind thickness measurement. The methods used to automatically select the terminal endpoint in step S1306 are discussed in more detail below. Note that the linear distance between the initial endpoint and the corresponding lung boundary point (the terminal endpoint) is displayed as the pleural thickness at that position. The line on which the pleural thickness is based is displayed on the interface, and if the line does not, in the opinion of the user, represent an accurate estimation of the pleural thickness at that position, the user may manually override the semi-automated measurement by relocating the terminal endpoint through the interface.

When the user has completed a scan (in either manual or semi-automated mode), a report of pleural space measurements is generated. In clinical practice, such a report could be annotated with selected images and included with the patient's clinical record. The potential for tracking changes of disease extent over time with such reports is a potentially powerful application of the present invention. The basic function of this interface is to provide a "window" that allows a radiologist or clinician to view all the images of a complete CT scan, make manual measurements of the mesothelioma tumor, and provide user input to the semi-automated measurement algorithms.

The graphical user interface thus has a display controller configured to display a representation of the extent of the pleural space and may include one or more control sections configured to perform various functions related to determining an extent of the pleural space. For example, the display controller has a first control section configured to display at least one measurement of the extent of the pleural space obtained by one or more observers. Moreover, the display controller has a second control section configured to display a plurality of measurements of the extent of the pleural space obtained at different times, and a third control section configured to compare a plurality of measurements of the extent of the pleural space obtained by multiple observers. In addition, the system includes a device configured to store the measurements of the extent of the pleural space obtained by the observers.

The graphical user interface was used in a clinical study to establish its utility as well as to illustrate the variability in human pleural space measurements and the need for the semi-automated approach of the present invention. The generally accepted approach to the manual measurement of mesothelioma in CT scans is based on a three-step process that involves (1) selection of a limited number of CT sections in which the disease is most prominent, (2) identification of specific locations within the selected sections that demonstrate the greatest pleural rind thickness, and (3) the actual measurement of tumor thickness at those locations. The variability in the third of these steps was measured; accordingly, the same locations within the same CT sections were presented to a set of observers so that variation in the actual tumor thickness measurements at fixed locations could be determined. Since no preferred sections or locations for mesothelioma measurement existed a priori, the first observer to participate in the study established the sections and locations used by all other observers.

Four observers (two attending radiologists and two attending oncologists) served as observers. The first observer ("Observer A") reviewed 22 CT scans on the interface described above. Observer A selected, for each scan, the three sections on which measurements would be made. Observer A then selected up to three measurement locations on each chosen section and performed the corresponding tumor measurements by constructing line segments specified by an initial endpoint and a terminal endpoint, both of which were selected by Observer A. Observer A was asked to construct the line segments such that the initial endpoints were along the chest wall or mediastinal aspect of the pleural rind and the terminal endpoints were along the visceral aspect of the pleural rind (effectively the lung boundary). This convention was adopted to accommodate the computerized methods, described below, which were designed to identify appropriate terminal endpoints along the lung boundary given initial endpoints input by a human observer.

These selected sections and initial endpoints served as the basis for the sessions of the other three observers. All observers after Observer A viewed the same 22 CT scans in random order through the interface. The scans reviewed by the other observers, however, indicated on the appropriate sections the initial endpoints chosen by Observer A; the actual line segments and terminal endpoints of Observer A were not shown. While the observers were able to view the complete scans, their task was to use the interface to select an appropriate terminal endpoint for each initial endpoint selected by Observer A. In effect, the task was as follows: given a specific location on a specific section, construct a line segment that most appropriately measures the thickness of the mesothelioma tumor at that location. Thus, variability of section and location selection was eliminated, and only variability of the actual mesothelioma measurement was captured. The observers were able to adjust their terminal endpoints, but the initial endpoints were fixed and unalterable.

The terminal endpoints and the lengths of the corresponding line segments were compared among all four observers. An "average length" was computed for each measurement, and the degrees of variability of each observer's lengths relative (1) to the average length at each measurement location and (2) to the lengths established by other observers at corresponding measurement locations were evaluated based on paired Student's t-tests. Statistically significant differences existed between the paired measurements made by two pair of observers (p<0.05). This study documented, for the first time, the level of inter-observer variability that exists in the current standard of clinical practice for quantitatively evaluating mesothelioma: manual, linear measurements of the pleural rind. This study underscores the necessity for consistent measurements: two pair of observers in this study recorded measurements of the same scans that differed to a statistically significant degree; therefore, the variability of measurements made by human observers could lead to false indications of tumor change. Such variability in measurements made on the same scan would only be exaggerated by the more clinically relevant comparison of measurements on temporally sequential scans.

In step S1306, the lung segmentation regions and the spatial positions of pixels along the lung segmentation contours are used to automatically identify terminal endpoints for each given initial endpoint. Six algorithms were used to identify terminal endpoints: (1) the "minimum-distance" algorithm, (2) the "local-maximum-distance" algorithm, (3) the "lung-region-radius" algorithm, (4) the "normal-to-lung-boundary" algorithm, (5) the "normal-to-initial-endpoint" algorithm, and (6) the "hybrid" algorithm. All six algorithms use the initial endpoint manually provided at each selected measurement location.

For a given initial endpoint, the minimum-distance algorithm selects as the terminal endpoint that pixel along the lung contour for which the Euclidean distance between the lung contour pixel and the initial endpoint is minimum.

The local-maximum-distance algorithm selects as the terminal endpoint the lung contour pixel with the greatest Euclidean distance from the given initial endpoint. The search for such a maximum-distance lung contour pixel is confined to a section of the lung contour in the vicinity of the initial endpoint.

The lung-region-radius algorithm selects as the terminal endpoint associated with a given initial endpoint the lung contour pixel that lies on the line connecting the initial endpoint with the center-of-mass of the lung segmentation region.

The normal-to-lung-boundary algorithm is based on the perpendicular distance between the initial endpoint and a line normal to the lung contour at a particular contour pixel. A lung contour pixel becomes a terminal endpoint candidate if its associated normal line extends within a predetermined pixel dimension of the initial endpoint. The predetermined pixel dimension is between 1 and 5 pixels, and in the preferred embodiment, one pixel. The candidate lung contour pixel that is most closely oriented with the lung region center-of-mass relative to the initial endpoint is then selected as the terminal endpoint.

The normal-to-initial-endpoint algorithm seeks to identify a line that is, in some sense, "tangent" to the local anatomy at the initial endpoint pixel (i.e., effectively tangent to the outer tumor border). To define this tangent line, a series of lines centered at the initial endpoint and oriented at different angles is constructed. The standard deviations of the gray levels of a predefined number of pixels along these multiple lines are computed. The line yielding the smallest standard deviation is selected as the tangent line. Next, the line normal to this tangent line is constructed, and the lung contour pixel intercepted by this normal line is chosen as the corresponding terminal endpoint.

Finally, the hybrid algorithm selects as the appropriate measurement the line segment associated with the median angle of orientation of the line segments generated by the other five algorithms.

Figure 14:
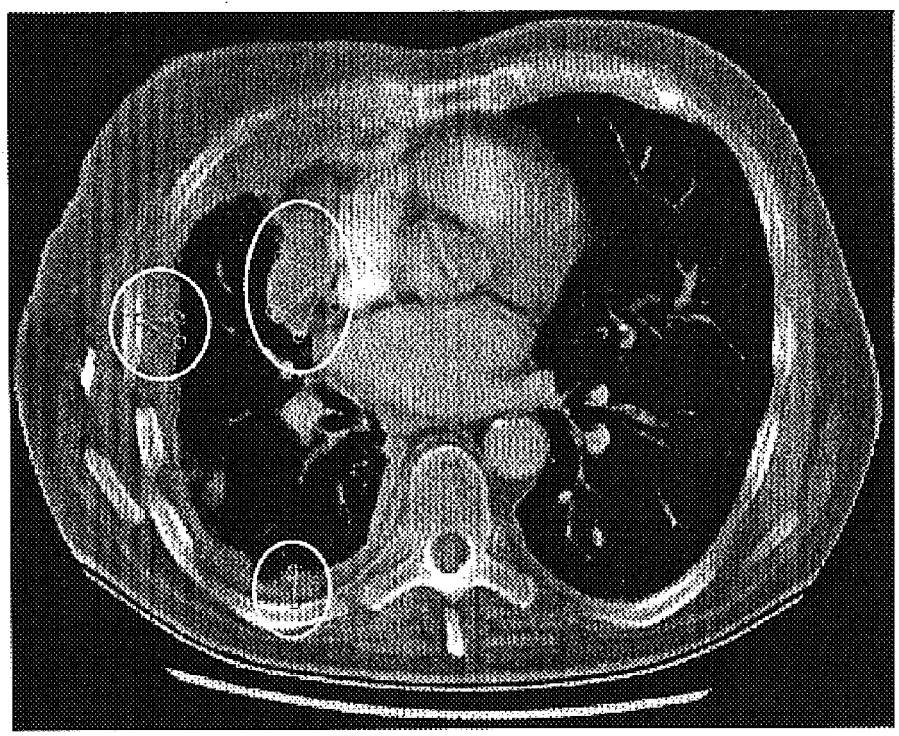
FIG. 14 illustrates mesothelioma measurements generated by six semi-automated measurement algorithms at each of three user-defined locations.

FIG. 14 shows the interface with mesothelioma measurements that were made through the semi-automated techniques; the six algorithms described above were used to connect the user-selected initial endpoints (along the chest wall and mediastinal boundary) with points along the lung boundary. In a preliminary study of 22 CT scans from 22 different mesothelioma patients, the mesothelioma measurements generated by these six semi-automated algorithms based on 134 manually selected initial endpoints closely approximated the average measurements of four human observers at the same 134 location. Of the 804 total semi-automated measurements (six algorithms applied to each of 134 initial endpoints), 671 (83.5%) were within 15% of the corresponding average manual measurements. The hybrid and local maximum algorithms yielded the best performance overall, with 121 (90.3%) and 116 (86.6%) of the 134 measurements from these two algorithms, respectively, falling within 15% of the corresponding average manual measurements (see Table I).

The results shown in Table I demonstrate that semi-automated methods are capable of consistently replicating measurements made by human observers, at least within the range of variability inherent among these observers.

Finally, in step S1308, the linear distance is measured based on (1) the location of the initial endpoint pixel selected in step S1304 and (2) the terminal endpoint pixel computed in step S1306 using one of the six algorithms described above.

Figure 15:
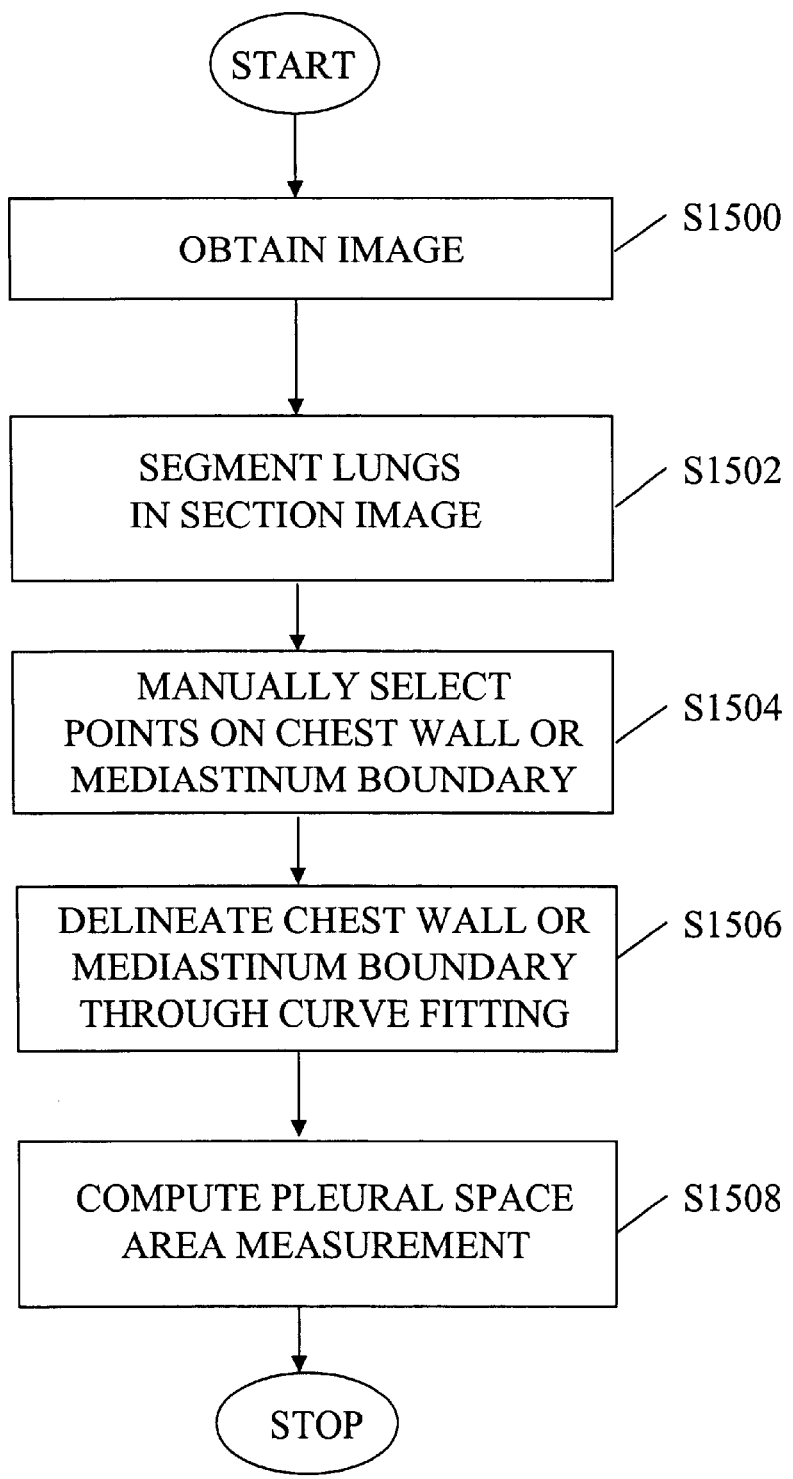
FIG. 15 illustrates a fifth embodiment of the present invention, in which the geometric area of mesothelioma is computed using a semi-automated approach.

FIG. 15 illustrates a fifth embodiment of the present invention, in which the area of mesothelioma, instead of a number of linear measurements, is computed in relevant sections. Such an area-based approach yields information that more completely represents the extent of disease and more fully utilizes the volumetric data acquired by CT scans. It is essential to recognize that the area-based approach becomes a volumetric approach in the limit when the area-based approach is implemented in all CT sections in which mesothelioma is demonstrated. The manual implementation of an area-based measurement approach requires an observer to outline the mesothelioma tumor on a CT section. Since this approach is extremely tedious and impractical, a semi-automated approach to mesothelioma area calculations has been developed based on the number of pixels that lie between the lung boundary and the chest wall and mediastinum boundaries. The number of pixels within this region is multiplied by the pixel dimension (obtained from the DICOM header) to obtain area in real-world units (square millimeters). Since the present automated lung segmentation method already provides the lung boundary, delineation of the chest wall and mediastinum boundaries must be accomplished. The semi-automated area-based approach, therefore, is based on the fully automated delineation of the lung boundary and the semi-automated delineation of the chest wall and mediastinum boundaries.

The overall scheme includes an initial acquisition of CT image data in step S1500, which is identical to image acquisition step S100 described above with regard to FIGS. 1, 9A, and 10. Next, for each section image, gray-level thresholding techniques are used to segment the lungs in step S1502. Again, note that step S1502 is identical to the lung segmenting step S102 described above with regard to FIGS. 2A and 2B.

For step S1504, the graphical user interface described above has been modified to accept a series of points that a user identifies along the chest wall and mediastinum.

In step S1506, a curve representing the chest wall and mediastinum boundaries is estimated between the selected points using interpolation (e.g., cubic spline interpolation). Since the result of interpolation depends on the number of data points used and the density of their spacing (as selected by the user), the accuracy of the resulting delineation of the chest wall and mediastinum depends on these factors; in particular, an accurate delineation requires fewer user-input points along sections of low chest wall curvature and requires more user-input points along sections of more pronounced curvature.

A cubic-spline-interpolated delineation is based on only a few points as a coarse approximation to the chest wall and mediastinum boundaries. Such a coarse delineation serves as a guide to locating the actual boundary although other interpolation techniques can similarly be used. At each point along the coarse delineated contour, a line perpendicular to the contour at that point is constructed; the first derivative of pixel values along this line is analyzed to identify the point of transition between the chest wall or mediastinum and the mesothelioma tumor. The set of pixels identified in this manner form the chest wall and mediastinum boundaries.

Finally, in step S1508, the area of mesothelioma is computed from the number of pixels within the set defined by the exclusive-OR (XOR) operation between the set of pixels enclosed by the lung contour and the set of pixels enclosed by the lung and mediastinum contour (with the assumption that the set of pixels enclosed by the lung contour is a subset of the set of pixels enclosed by the lung and mediastinum contour).

Figure 16:
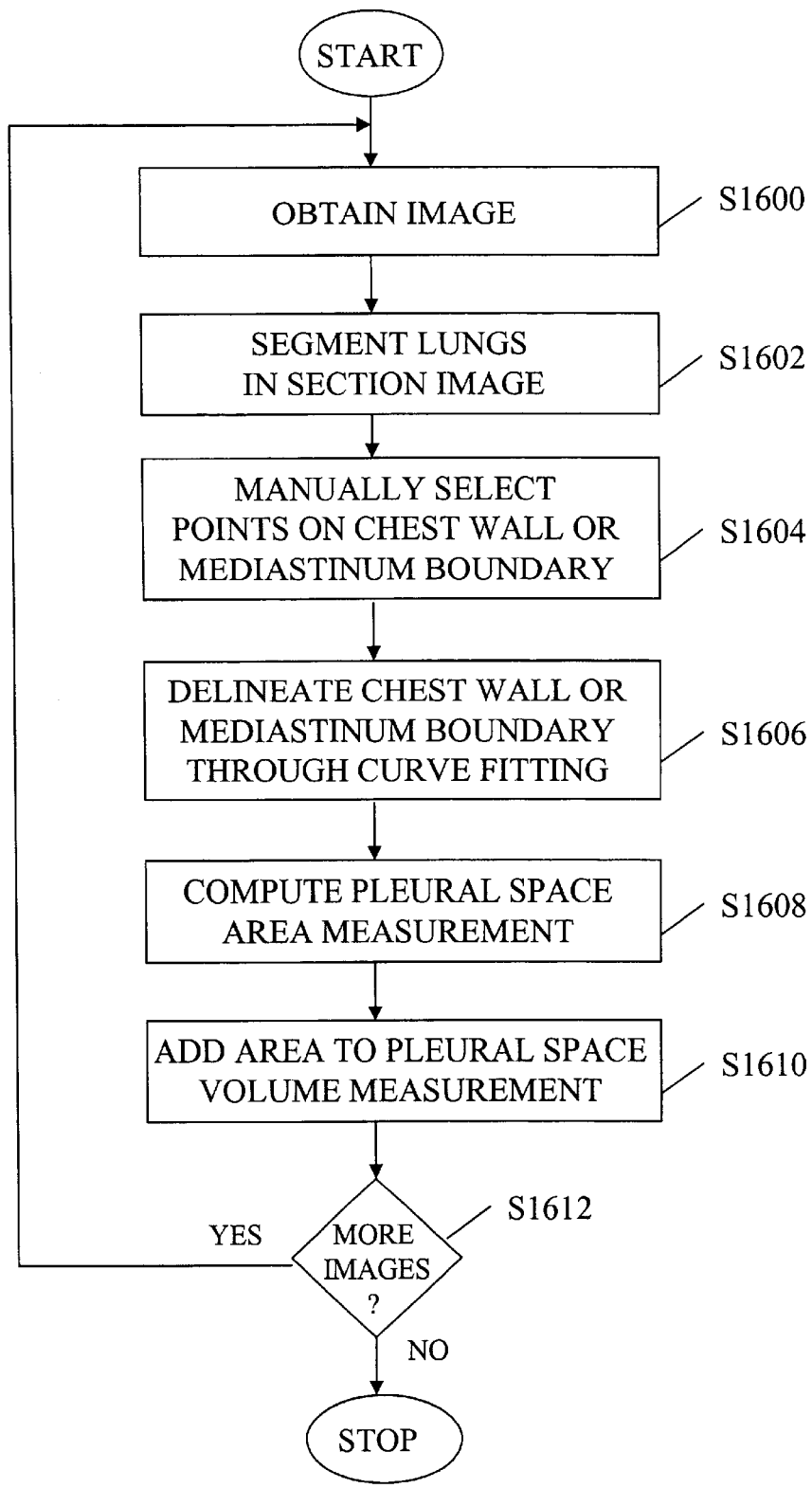
FIG. 16 illustrates a sixth embodiment of the present invention, in which the volume of mesothelioma is computed using a semi-automated approach.

FIG. 16 is a flowchart of still another embodiment of the present invention in which the complete volume of the pleural space and/or the pleural thickening is calculated using the semi-automated method described with regard to FIG. 15. Steps 1600–1608 of FIG. 16 are the same as steps 1500–1508 of FIG. 15, while step S1610 sums the pleural area measurements computed for each CT image, and step S1612 checks if all CT images have been evaluated.

The method of the present invention demonstrates promising performance in its ability to accurately segment the lungs, delineate the chest wall based on rib segmentation, and quantify the pleural space and/or the pleural thickening in CT scans. The invention allows radiologists to procure many measurements of a patient's mesothelioma with minimal effort. With the semi-automated rib-identification technique, the distance between any number of ribs and the corresponding lung in any number of CT sections can be calculated quickly and efficiently. In addition, the fully automated technique for the quantitative evaluation of mesothelioma, without user interaction, identifies the lung boundary, identifies the chest wall border as represented by the ribs, and provides measures of the distance between the two borders as an assessment of the pleural-space thickening associated with mesothelioma. Such tools are expected to greatly enhance the utility of CT scans in the management of mesothelioma patients.

Other diseases also manifest in the pleural space, most notably pleural effusions, diffuse pleural thickening, pleural plaques, empyema, and pleural metastasis (see Reference 10). Consequently, the present invention is applicable to the evaluation of a wide range of pathologies that increase the size of the pleural space (i.e., the region between the visceral and parietal pleural, which, in the absence of disease, are in direct contact with each other) or cause pleural thickening.

Furthermore, this automated method for measuring the pleural space and/or the pleural thickening has application as part of an ensemble of computer-aided diagnostic methods that may be applied to thoracic CT, MR, or ultrasound scans. In addition to techniques designed to evaluate CT, MR, or ultrasound scans for the presence of lung nodules, emphysema, and pulmonary embolus, for example, this technique for measuring the pleural space could indicate to a radiologist the potential presence of pleura-based disease in one or both of the patient's hemithoraces. The method could compare the pleural space measures of the two hemithoraces in a scan to determine the likelihood of the presence of pleura-based disease. Alternatively, the method could be trained on a large number of normal scans to develop a statistical model of pleural-space measurements in the absence of disease and use this model to calculate the likelihood of disease in novel cases.

Figure 11:
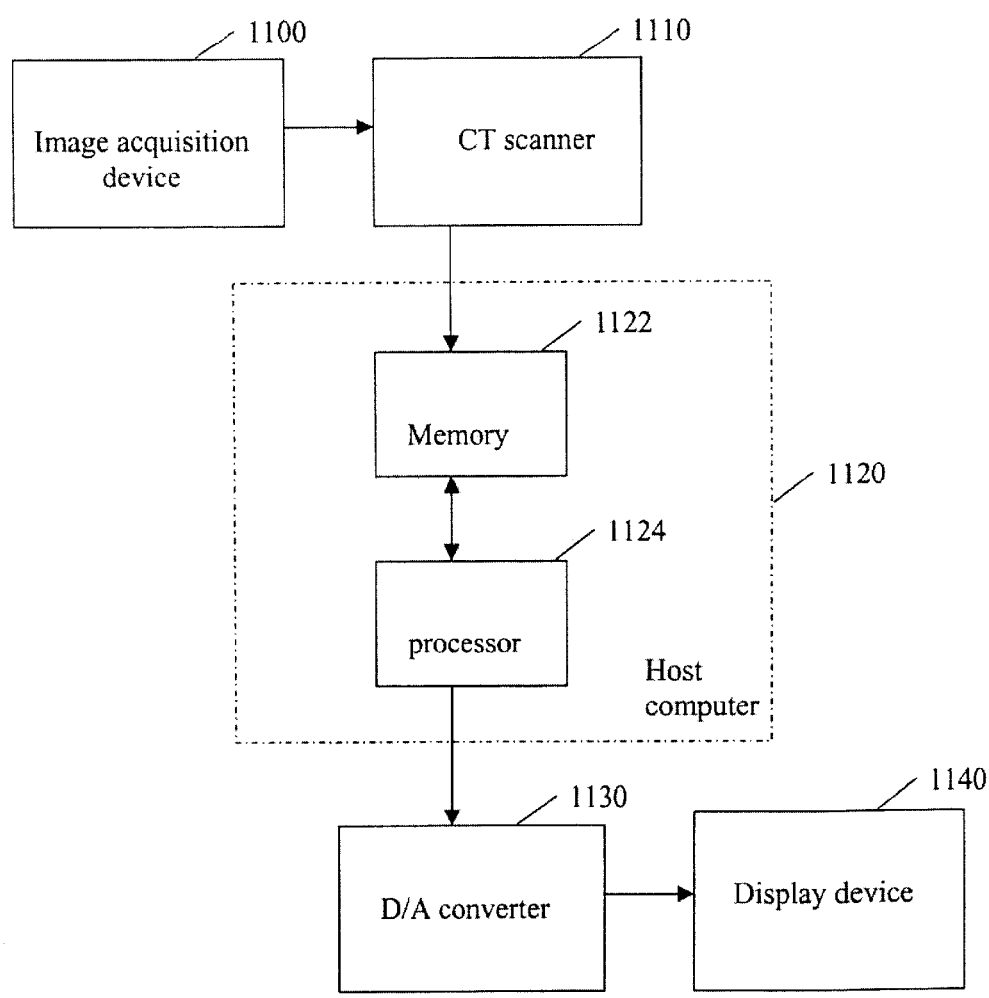
FIG. 11 is a block diagram illustrating a system implementing the present invention for the automated measurement of the pleural space and/or the pleural thickening in thoracic CT or MR scans.

FIG. 11 shows an exemplary system used to implement the embodiments of the present invention. In FIG. 11, CT images of an object are obtained from an image acquisition device 1100 followed by a CT scanner 1110. The CT images from the CT scanner 1110 are input to a host computer 1120. Alternatively, the image data may be retrieved from an existing database via PACS (Picture Archiving Communication System). In the host computer 1120, each CT image is put into memory 1122. Upon processing to find the pleural space measurement from the CT images, the CT image data is passed to a processor 1124 where the lungs are segmented out according to the steps of FIG. 2A, the ribs are then segmented out by constructing a chest wall image according to the steps of FIG. 3A and using either the semi-automated or fully automated mode, and the lung and rib segmentation results are used to calculate the pleural space measurements which are either superimposed onto images, stored in file format, or given in text format. The results are then displayed on the display device 1140 after passing through a digital-to-analog converter 1130.

This invention conveniently may be implemented using a conventional general purpose computer or micro-processor programmed according to the teachings of the present invention, as will be apparent to those skilled in the computer art. Appropriate software can readily be prepared by programmers of ordinary skill based on the teachings of the present disclosure, as will be apparent to those skilled in the software art.

Figure 12:
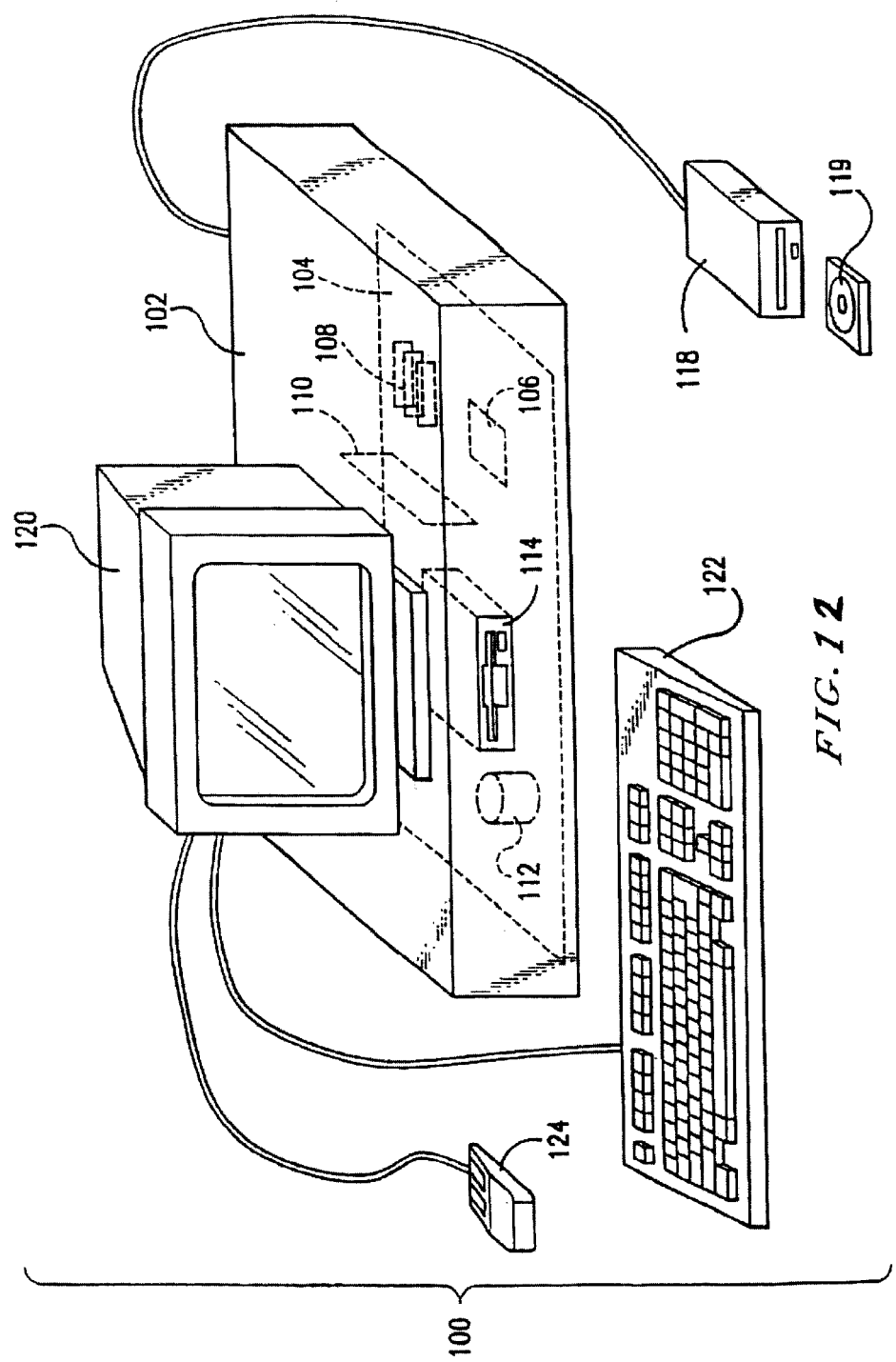
FIG. 12 is an exemplary general purpose computer programmed according to the teachings of the present invention.

FIG. 12 is a schematic illustration of a computer system for the computerized assessment of pleural disease. A computer 100 implements the method of the present invention, wherein the computer housing 102 houses a motherboard 104 which contains a CPU 106, memory 108 (e.g., DRAM, ROM, EPROM, EEPROM, SRAM, SDRAM, and Flash RAM), and other optional special purpose logic devices (e.g., ASICs) or configurable logic devices (e.g., GAL and reprogrammable FPGA). The computer 100 also includes plural input devices, (e.g., a keyboard 122 and mouse 124), and a display card 110 for controlling monitor 120. In addition, the computer 100 further includes a floppy disk drive 114; other removable media devices (e.g., compact disc 119, tape, and removable magneto-optical media (not shown)); and a hard disk 112, or other fixed, high density media drives, connected using an appropriate device bus (e.g., a SCSI bus, an Enhanced IDE bus, or a Ultra DMA bus). Also connected to the same device bus or another device bus, the computer 100 may additionally include a compact disc reader 118, a compact disc reader/writer unit (not shown) or a compact disc jukebox (not shown). Although compact disc 119 is shown in a CD caddy, the compact disc 119 can be inserted directly into CD-ROM drives which do not require caddies.

As stated above, the system includes at least one computer readable medium. Examples of computer readable media are compact discs 119, hard disks 112, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling both the hardware of the computer 100 and for enabling the computer 100 to interact with a human user. Such software may include, but is not limited to, device drivers, operating systems and user applications, such as development tools. Such computer readable media further includes the computer program product of the present invention for performing the inventive method of the present invention. The computer code devices of the present invention can be any interpreted or executable code mechanism, including but not limited to scripts, interpreters, dynamic link libraries, Java classes, and complete executable programs. Moreover, parts of the processing of the present invention may be distributed for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

Numerous modifications and variations of the present invention are possible in light of the above teachings. It is therefore to be understood that within the scope of the appended claims, the invention may be practiced otherwise than as specifically described herein.

TABLE I

Preliminary results of six semi-automated mesothelioma algorithms based on manually selected initial endpoints at 134 measurement locations in a database of 22 CT scans. The numbers in each colunm represent the percentage of measurements obtained from each method that deviate from the average manual measurement by less than the percentage specified at the top of each column.

| Semi-Automated Algorithm | Deviation <10% | Deviation <15% | Deviation <20% |
| --- | --- | --- | --- |
| minimum distance | 63% (85/134) | 84% (113/134) | 94% (126/134) |
| local-maximum distance | 66% (89/134) | 87% (116/134) | 94% (126/134) |
| lung-region radius | 62% (83/134) | 77% (103/134) | 86% (115/134) |
| normal to lung boundary | 71% (95/134) | 83% (111/134) | 92% (123/134) |
| normal to initial endpoint | 69% (92/134) | 80% (107/134) | 89% (119/134) |
| hybrid | 73% (98/134) | 90% (121/134) | 93% (125/134) |
| Total | 67% (542/804) | 83% (671/804) | 91% (734/804) |

What is claimed as new and desired to be secured by Letters Patent of the United States is:

1. A method for determining an extent of at least one of a pleural space and a pleural thickening, comprising:
    obtaining an image including at least one of the pleural space and the pleural thickening;
    segmenting at least one lung in the obtained image;
    obtaining an initial endpoint on one of a chest wall and a mediastinum boundary;
    determining a terminal endpoint on a boundary of the at least one segmented lung; and
    determining a distance between said initial endpoint and said terminal endpoint as the extent of the at least one of the pleural space and the pleural thickening.

2. The method of claim 1, wherein the step of determining a terminal endpoint comprises:
    selecting, as the terminal endpoint, a pixel on the boundary of the at least one segmented lung for which a distance between the pixel and the initial endpoint is minimum.

3. The method of claim 1, wherein the step of determining a terminal endpoint comprises:
    selecting, as the terminal endpoint, a pixel on the boundary of the at least one segmented lung for which a distance between the pixel and the initial endpoint is maximum,
    the pixel being located within a predetermined distance of the initial endpoint.

4. The method of claim 1, wherein the step of determining a terminal endpoint comprises:
    selecting, as the terminal endpoint, a pixel on the boundary of the at least one segmented lung that lies on a line connecting the initial endpoint with a center-of-mass of the at least one segmented lung.

5. The method of claim 1, wherein the step of determining a terminal endpoint comprises:
    determining as a set of candidate terminal endpoints those pixels on the boundary of the at least one segmented lung having an associated normal line that extends within a predetermined number of pixels of the initial endpoint; and
    selecting, as the terminal endpoint, a pixel from the set of candidate terminal endpoints for which the associated normal line is most closely aligned with a line from the initial endpoint to a center-of-mass of the at least one segmented lung.

6. The method of claim 1, wherein the step of determining a terminal endpoint comprises:
    constructing a set of lines passing through the initial endpoint at different angles;
    determining a standard deviation of gray levels of a predetermined number of pixels on each line in the set of lines;
    selecting, as a tangent line, a line in the set of lines having a smallest standard deviation, as determined in the preceding determining step; and
    selecting, as the terminal endpoint, a pixel on the boundary of the at least one segmented lung that lies on a line normal to the tangent line selected in the preceding selecting step.

7. The method of claim 1, wherein the obtaining step comprises:
    obtaining a computed-tomographic image including at least one of the pleural space and the pleural thickening.

8. The method of claim 1, wherein the obtaining step comprises:
    obtaining a magnetic resonance image including at least one of the pleural space and the pleural thickening.

9. A system configured to determine an extent of at least one of a pleural space and a pleural thickening by performing the steps recited in claim 1.

10. The system of claim 9, further comprising a graphical user interface (GUI).

11. The system of claim 10, wherein the GUI comprises:
a display controller configured to display a representation of the extent of the at least one of the pleural space and the pleural thickening.

12. The system of claim 11, wherein the display controller comprises:
a first control section configured to display at least one measurement of the extent of the at least one of the pleural space and the pleural thickening obtained by at least one observer.

13. The system of claim 12, further comprising:
a device configured to store the at least one measurement of the extent of the at least one of the pleural space and the pleural thickening obtained by at least one observer.

14. The system of claim 11, wherein the display controller comprises:
a second control section configured to display a plurality of measurements of the extent of the at least one of the pleural space and the pleural thickening obtained at a plurality of different times.

15. The system of claim 11, wherein the display controller comprises:
a third control section configured to compare a plurality of measurements of the extent of the at least one of the pleural space and the pleural thickening obtained by a plurality of observers.

16. The system of claim 9, further comprising:
a display configured to display a representation of the extent of the at least one of the pleural space and the pleural thickening.

17. A method for determining an extent of at least one of a pleural space and a pleural thickening, comprising:
obtaining an image including at least one of the pleural space and the pleural thickening;
segmenting at least one lung in the obtained image;
selecting at least two pixels, each of the two pixels being on one of a chest wall and a mediastinum boundary;
determining a contour passing through the at least two pixels; and
calculating an area between a boundary of the at least one segmented lung and the contour as the extent of the at least one of the pleural space and the pleural thickening.

18. The method of claim 17, further comprising:
initializing a volume to zero;
adding the area calculated in the calculating step to the volume;
repeating the obtaining, segmenting, selecting, determining, calculating, and adding steps for each image in a set of images; and
outputting the volume as the extent of the at least one of the pleural space and the pleural thickening.

19. A method for determining an extent of at least one of a pleural space and a pleural thickening, comprising the steps of:
obtaining an image including at least one of the pleural space and the pleural thickening;
segmenting lungs in the obtained image;
constructing a chest wall image from the obtained image using a lung boundary obtained in the segmenting step and a series of normal rays extending away from the lung boundary;
identifying ribs in the chest wall image;
mapping a location of the identified ribs back into the obtained image; and
determining in the obtained image the extent of the at least one of the pleural space and the pleural thickening between the identified ribs mapped back to the obtained image and at least one segmented lung.

20. The method of claim 19, wherein the constructing step comprises:
identifying anterior- and posterior-most pixels along the lung boundary of the at least one segmented lung;
constructing the series of normal rays originating on the lung boundary nearest a chest wall between the anterior- and posterior-most pixels, and extending in a normal direction away from the lung boundary; and
constructing the chest wall image as columns of pixels intercepted by the series of normal rays.

21. A computer program product storing program instructions for execution on a computer system, which when executed by the computer system, cause the computer system to perform the method recited in any one of claims 1–20.

22. A system configured to determine an extent of at least one of a pleural space and a pleural thickening by performing the steps recited in any one of claims 2–20.

* * * * *

UNITED STATES PATENT AND TRADEMARK OFFICE
CERTIFICATE OF CORRECTION

PATENT NO.   : 6,813,375 B2
DATED        : November 2, 2004
INVENTOR(S)  : Samuel G. Armato III et al.

It is certified that error appears in the above-identified patent and that said Letters Patent is hereby corrected as shown below:

Title page,
Item [57], ABSTRACT,
Line 8, change "boundar" to -- boundary --;
Line 11, delete "the" (first occurrence).

Column 2,
Line 16, change "Monnieir" to -- Monnier --.

Column 12,
Line 59, delete "and".

Column 14,
Line 2, delete ",".

Column 17,
Lines 32 and 34, change "lung" to -- chest wall --.

Signed and Sealed this

Fifteenth Day of March, 2005

JON W. DUDAS
*Director of the United States Patent and Trademark Office*

UNITED STATES PATENT AND TRADEMARK OFFICE
CERTIFICATE OF CORRECTION

Page 1 of 1

PATENT NO.      : 6,813,375 B2
APPLICATION NO. : 10/292625
DATED           : November 2, 2004
INVENTOR(S)     : Samuel G. Armato, III et al.

It is certified that error appears in the above-identified patent and that said Letters Patent is hereby corrected as shown below:

In the Specifications:

Column 1, delete lines 13-16, and insert --This invention was made with U.S. Government support under grant number CA 083908 awarded by the National Institutes of Health (NIH). The U.S. Government has certain rights in the invention.--

Signed and Sealed this
Eighteenth Day of September, 2012

David J. Kappos
*Director of the United States Patent and Trademark Office*